(12) United States Patent
Seguin

(10) Patent No.: US 7,682,390 B2
(45) Date of Patent: Mar. 23, 2010

(54) ASSEMBLY FOR SETTING A VALVE PROSTHESIS IN A CORPOREAL DUCT

(75) Inventor: Jacques Seguin, The Friary (GB)

(73) Assignee: Medtronic, Inc., Minneapolis, MN (US)

( * ) Notice: Subject to any disclaimer, the term of this patent is extended or adjusted under 35 U.S.C. 154(b) by 759 days.

(21) Appl. No.: 10/484,865

(22) PCT Filed: Jul. 30, 2002

(86) PCT No.: PCT/FR02/02745

§ 371 (c)(1),
(2), (4) Date: Sep. 22, 2004

(87) PCT Pub. No.: WO03/011195

PCT Pub. Date: Feb. 13, 2003

(65) Prior Publication Data

US 2005/0033398 A1   Feb. 10, 2005

(30) Foreign Application Priority Data

Jul. 31, 2001   (FR) .................................. 01 10281

(51) Int. Cl.
*A61F 2/24* (2006.01)
(52) U.S. Cl. .................... 623/2.18; 623/1.26; 623/2.17; 623/2.14
(58) Field of Classification Search ................ 623/1.24, 623/1.26, 1.13, 1.25; *A61F 02/06*
See application file for complete search history.

(56) References Cited

U.S. PATENT DOCUMENTS

| 3,334,629 A | 8/1967 | Cohn |
| 3,409,013 A | 11/1968 | Berry |
| 3,540,431 A | 11/1970 | Mobin-Uddin |
| 3,587,115 A | 6/1971 | Shiley |
| 3,628,535 A | 12/1971 | Ostrowsky et al. |
| 3,642,004 A | 2/1972 | Osthagen et al. |

(Continued)

FOREIGN PATENT DOCUMENTS

EP     850607 A1 *   7/1998

(Continued)

OTHER PUBLICATIONS

US Patent Application Publication 2001/0,002,455—Vesely (Published Mar. 31, 2001).

(Continued)

*Primary Examiner*—Corrine M McDermott
*Assistant Examiner*—Jason-Dennis Stewart
(74) *Attorney, Agent, or Firm*—Mike Jaro; Jeffrey J. Hohenshell

(57) ABSTRACT

The invention concerns an assembly comprising a valve prosthesis to be implanted and a support receiving said valve. The support comprises: at least a tubular portion made of a pliable material slightly stretchable in the circumferential direction; means for fixing said tubular portion to the wall of the corporeal duct; and a plurality of elongated reinforcing elements, arranged on the circumference of said tubular portion and linked to said tubular portion independently of one another; the valve is linked at least partly to said elongated reinforcing elements, in particular at the commissures of its leaflets, and said elongated reinforcing elements jointly form, in extended position, a structure having a predetermined diameter that ensures sufficient extension of said valve.

30 Claims, 10 Drawing Sheets

U.S. PATENT DOCUMENTS

| | | | |
|---|---|---|---|
| 3,657,744 | A | 4/1972 | Ersek |
| 3,671,979 | A | 6/1972 | Moulopoulos |
| 3,714,671 | A | 2/1973 | Edwards et al. |
| 3,755,823 | A | 9/1973 | Hancock |
| 3,795,246 | A | 3/1974 | Sturgeon |
| 3,839,741 | A | 10/1974 | Haller |
| 3,868,956 | A | 3/1975 | Alfidi et al. |
| 3,874,388 | A | 4/1975 | King et al. |
| 4,035,849 | A | 7/1977 | Angell et al. |
| 4,056,854 | A | 11/1977 | Boretos et al. |
| 4,106,129 | A | 8/1978 | Carpentier et al. |
| 4,222,126 | A | 9/1980 | Boretos et al. |
| 4,233,690 | A | 11/1980 | Akins |
| 4,265,694 | A | 5/1981 | Boretos |
| 4,291,420 | A | 9/1981 | Reul |
| 4,297,749 | A | 11/1981 | Davis et al. |
| 4,339,831 | A | 7/1982 | Johnson |
| 4,343,048 | A | 8/1982 | Ross et al. |
| 4,345,340 | A | 8/1982 | Rosen |
| 4,425,908 | A | 1/1984 | Simon |
| 4,470,157 | A | 9/1984 | Love |
| 4,501,030 | A | 2/1985 | Lane |
| 4,574,803 | A | 3/1986 | Storz |
| 4,580,568 | A | 4/1986 | Gianturco |
| 4,592,340 | A | 6/1986 | Boyles |
| 4,610,688 | A | 9/1986 | Silvestrini et al. |
| 4,612,011 | A | 9/1986 | Kautzky |
| 4,647,283 | A | 3/1987 | Carpentier et al. |
| 4,648,881 | A | 3/1987 | Carpentier et al. |
| 4,655,771 | A | 4/1987 | Wallsten |
| 4,662,885 | A | 5/1987 | DiPisa, Jr. |
| 4,665,906 | A | 5/1987 | Jervis |
| 4,681,908 | A | 7/1987 | Broderick et al. |
| 4,710,192 | A | 12/1987 | Liotta et al. |
| 4,733,665 | A | 3/1988 | Palmaz |
| 4,777,951 | A | 10/1988 | Cribier et al. |
| 4,787,899 | A | 11/1988 | Lazarus |
| 4,787,901 | A | 11/1988 | Baykut |
| 4,796,629 | A | 1/1989 | Grayzel |
| 4,797,901 | A | 1/1989 | Baykut |
| 4,819,751 | A | 4/1989 | Shimada et al. |
| 4,834,755 | A | 5/1989 | Silvestrini et al. |
| 4,856,516 | A | 8/1989 | Hillstead |
| 4,872,874 | A | 10/1989 | Taheri |
| 4,878,495 | A | 11/1989 | Grayzel |
| 4,878,906 | A | 11/1989 | Lindemann et al. |
| 4,883,458 | A | 11/1989 | Shiber |
| 4,909,252 | A | 3/1990 | Goldberger |
| 4,917,102 | A | 4/1990 | Miller et al. |
| 4,922,905 | A | 5/1990 | Strecker |
| 4,954,126 | A | 9/1990 | Wallsten |
| 4,966,604 | A | 10/1990 | Reiss |
| 4,979,939 | A | 12/1990 | Shiber |
| 4,986,830 | A | 1/1991 | Owens et al. |
| 4,994,077 | A | 2/1991 | Dobben |
| 5,002,559 | A | 3/1991 | Tower |
| 5,007,896 | A | 4/1991 | Shiber |
| 5,026,366 | A | 6/1991 | Leckrone |
| 5,032,128 | A | 7/1991 | Alonso |
| 5,037,434 | A | 8/1991 | Lane |
| 5,047,041 | A | 9/1991 | Samuels |
| 5,059,177 | A | 10/1991 | Towne et al. |
| 5,061,273 | A | 10/1991 | Yock |
| 5,085,635 | A | 2/1992 | Cragg |
| 5,089,015 | A | 2/1992 | Ross |
| 5,152,771 | A | 10/1992 | Sabbaghian et al. |
| 5,161,547 | A | 11/1992 | Tower |
| 5,163,953 | A | 11/1992 | Vince |
| 5,167,628 | A | 12/1992 | Boyles |
| 5,217,483 | A | 6/1993 | Tower |
| 5,232,445 | A | 8/1993 | Bonzel |
| 5,272,909 | A | 12/1993 | Nguyen et al. |
| 5,295,958 | A | 3/1994 | Shturman |
| 5,327,774 | A | 7/1994 | Nguyen et al. |
| 5,332,402 | A | 7/1994 | Teitelbaum |
| 5,350,398 | A | 9/1994 | Pavcnik et al. |
| 5,370,685 | A | 12/1994 | Stevens |
| 5,389,106 | A | 2/1995 | Tower |
| 5,397,351 | A | 3/1995 | Pavcnik et al. |
| 5,411,055 | A | 5/1995 | Andersen et al. |
| 5,415,633 | A | 5/1995 | Lazarus et al. |
| 5,431,676 | A | 7/1995 | Dubrul et al. |
| 5,443,446 | A | 8/1995 | Shturman |
| 5,480,424 | A | 1/1996 | Cox |
| 5,489,294 | A | 2/1996 | McVenes et al. |
| 5,489,297 | A | 2/1996 | Duran |
| 5,496,346 | A | 3/1996 | Horzewski et al. |
| 5,500,014 | A | 3/1996 | Quijano et al. |
| 5,507,767 | A | 4/1996 | Maeda et al. |
| 5,545,209 | A | 8/1996 | Roberts et al. |
| 5,545,211 | A | 8/1996 | An et al. |
| 5,545,214 | A | 8/1996 | Stevens |
| 5,554,185 | A | 9/1996 | Block et al. |
| 5,575,818 | A | 11/1996 | Pinchuk |
| 5,580,922 | A | 12/1996 | Park et al. |
| 5,591,195 | A | 1/1997 | Taheri et al. |
| 5,609,626 | A | 3/1997 | Quijano et al. |
| 5,645,559 | A | 7/1997 | Hachtman et al. |
| 5,665,115 | A | 9/1997 | Cragg |
| 5,667,523 | A | 9/1997 | Bynon et al. |
| 5,674,277 | A | 10/1997 | Freitag |
| 5,695,498 | A | 12/1997 | Tower |
| 5,702,368 | A | 12/1997 | Stevens et al. |
| 5,713,953 | A | 2/1998 | Vallana et al. |
| 5,716,417 | A | 2/1998 | Girard et al. |
| 5,746,709 | A * | 5/1998 | Rom et al. .................. 604/8 |
| 5,749,890 | A | 5/1998 | Shaknovich |
| 5,766,151 | A | 6/1998 | Valley et al. |
| 5,782,809 | A | 7/1998 | Umeno et al. |
| 5,800,456 | A | 9/1998 | Maeda et al. |
| 5,800,508 | A | 9/1998 | Goicoechea et al. |
| 5,817,126 | A | 10/1998 | Imran |
| 5,824,041 | A | 10/1998 | Lenker |
| 5,824,043 | A | 10/1998 | Cottone, Jr. |
| 5,824,053 | A | 10/1998 | Khosravi et al. |
| 5,824,056 | A | 10/1998 | Rosenberg |
| 5,824,061 | A | 10/1998 | Quijano et al. |
| 5,824,064 | A | 10/1998 | Taheri |
| 5,840,081 | A | 11/1998 | Andersen et al. |
| 5,843,158 | A | 12/1998 | Lenker et al. |
| 5,855,597 | A | 1/1999 | Jayaraman |
| 5,855,601 | A | 1/1999 | Bessler et al. |
| 5,860,996 | A | 1/1999 | Tower |
| 5,861,028 | A | 1/1999 | Angell |
| 5,868,783 | A | 2/1999 | Tower |
| 5,876,448 | A | 3/1999 | Thompson et al. |
| 5,888,201 | A | 3/1999 | Stinson et al. |
| 5,891,191 | A | 4/1999 | Stinson |
| 5,906,619 | A | 5/1999 | Olson et al. |
| 5,907,893 | A | 6/1999 | Zadno-Azizi et al. |
| 5,913,842 | A | 6/1999 | Boyd et al. |
| 5,925,063 | A | 7/1999 | Khosravi |
| 5,944,738 | A | 8/1999 | Amplatz et al. |
| 5,954,766 | A | 9/1999 | Zadno-Azizi et al. |
| 5,957,949 | A | 9/1999 | Leonhardt et al. |
| 5,968,068 | A | 10/1999 | Dehdashtian et al. |
| 5,984,957 | A | 11/1999 | Laptewicz, Jr. et al. |
| 5,997,573 | A | 12/1999 | Quijano et al. |
| 6,022,370 | A | 2/2000 | Tower |
| 6,027,525 | A | 2/2000 | Suh et al. |
| 6,029,671 | A | 2/2000 | Stevens et al. |
| 6,042,589 | A | 3/2000 | Marianne |
| 6,042,598 | A | 3/2000 | Tsugita et al. |
| 6,042,607 | A * | 3/2000 | Williamson et al. ........ 623/2.11 |

| | | | |
|---|---|---|---|
| 6,051,104 A | 4/2000 | Jang | |
| 6,059,809 A | 5/2000 | Amor et al. | |
| 6,110,201 A | 8/2000 | Quijano et al. | |
| 6,146,366 A | 11/2000 | Schachar | |
| 6,159,239 A | 12/2000 | Greenhalgh | |
| 6,162,208 A | 12/2000 | Hipps | |
| 6,162,245 A | 12/2000 | Jayaraman | |
| 6,168,614 B1 | 1/2001 | Andersen et al. | |
| 6,171,335 B1 | 1/2001 | Wheatley et al. | |
| 6,200,336 B1 | 3/2001 | Pavcnik et al. | |
| 6,203,550 B1 | 3/2001 | Olson | |
| 6,210,408 B1 | 4/2001 | Chandrasekaran et al. | |
| 6,218,662 B1 | 4/2001 | Tchakarov et al. | |
| 6,221,006 B1 | 4/2001 | Dubrul et al. | |
| 6,221,091 B1 | 4/2001 | Khosravi | |
| 6,241,757 B1 | 6/2001 | An et al. | |
| 6,245,102 B1 | 6/2001 | Jayaraman | |
| 6,254,642 B1 * | 7/2001 | Taylor | 623/23.64 |
| 6,258,114 B1 | 7/2001 | Konya et al. | |
| 6,258,115 B1 | 7/2001 | Dubrul | |
| 6,258,120 B1 | 7/2001 | McKenzie et al. | |
| 6,277,555 B1 | 8/2001 | Duran et al. | |
| 6,299,637 B1 | 10/2001 | Shaolian et al. | |
| 6,302,906 B1 | 10/2001 | Goicoechea et al. | |
| 6,309,382 B1 | 10/2001 | Garrison et al. | |
| 6,309,417 B1 | 10/2001 | Spence et al. | |
| 6,327,772 B1 | 12/2001 | Zadno-Azizi et al. | |
| 6,338,735 B1 | 1/2002 | Stevens | |
| 6,348,063 B1 | 2/2002 | Yassour et al. | |
| 6,350,277 B1 | 2/2002 | Kocur | |
| 6,352,708 B1 | 3/2002 | Duran et al. | |
| 6,371,935 B1 * | 4/2002 | Macoviak et al. | 604/43 |
| 6,371,970 B1 | 4/2002 | Khosravi et al. | |
| 6,371,983 B1 | 4/2002 | Lane | |
| 6,379,383 B1 | 4/2002 | Palmaz et al. | |
| 6,380,457 B1 | 4/2002 | Yurek et al. | |
| 6,398,807 B1 | 6/2002 | Chouinard et al. | |
| 6,409,750 B1 | 6/2002 | Hyodoh et al. | |
| 6,425,916 B1 | 7/2002 | Garrison et al. | |
| 6,440,164 B1 | 8/2002 | Di Matteo et al. | |
| 6,454,799 B1 | 9/2002 | Schreck | |
| 6,458,153 B1 * | 10/2002 | Bailey et al. | 623/1.24 |
| 6,461,382 B1 | 10/2002 | Cao | |
| 6,468,303 B1 | 10/2002 | Amplatz et al. | |
| 6,475,239 B1 | 11/2002 | Campbell et al. | |
| 6,482,228 B1 * | 11/2002 | Norred | 623/2.17 |
| 6,488,704 B1 | 12/2002 | Connelly et al. | |
| 6,494,909 B2 | 12/2002 | Greenhalgh | |
| 6,503,272 B2 * | 1/2003 | Duerig et al. | 623/1.24 |
| 6,508,833 B2 * | 1/2003 | Pavcnik et al. | 623/1.15 |
| 6,527,800 B1 | 3/2003 | McGuckin, Jr. et al. | |
| 6,530,949 B2 | 3/2003 | Konya et al. | |
| 6,530,952 B2 | 3/2003 | Vesely | |
| 6,562,031 B2 | 5/2003 | Chandrasekaran et al. | |
| 6,562,058 B2 | 5/2003 | Seguin et al. | |
| 6,569,196 B1 | 5/2003 | Vesely | |
| 6,585,758 B1 | 7/2003 | Chouinard et al. | |
| 6,592,546 B1 | 7/2003 | Barbut et al. | |
| 6,605,112 B1 | 8/2003 | Moll et al. | |
| 6,613,077 B2 | 9/2003 | Gilligan et al. | |
| 6,622,604 B1 | 9/2003 | Chouinard et al. | |
| 6,626,899 B2 * | 9/2003 | Houser et al. | 606/14 |
| 6,632,243 B1 | 10/2003 | Zadno-Azizi et al. | |
| 6,635,068 B1 | 10/2003 | Dubrul et al. | |
| 6,652,571 B1 | 11/2003 | White et al. | |
| 6,652,578 B2 * | 11/2003 | Bailey et al. | 623/1.24 |
| 6,656,213 B2 | 12/2003 | Solem | |
| 6,663,663 B2 | 12/2003 | Kim et al. | |
| 6,669,724 B2 | 12/2003 | Park et al. | |
| 6,673,089 B1 | 1/2004 | Yassour et al. | |
| 6,673,109 B2 | 1/2004 | Cox | |
| 6,676,698 B2 | 1/2004 | McGuckin, Jr. et al. | |
| 6,682,558 B2 | 1/2004 | Tu et al. | |
| 6,682,559 B2 | 1/2004 | Myers et al. | |
| 6,685,739 B2 | 2/2004 | DiMatteo et al. | |
| 6,689,144 B2 | 2/2004 | Gerberding | |
| 6,689,164 B1 | 2/2004 | Seguin | |
| 6,692,512 B2 | 2/2004 | Jang | |
| 6,692,513 B2 | 2/2004 | Streeter et al. | |
| 6,695,878 B2 | 2/2004 | McGuckin, Jr. et al. | |
| 6,702,851 B1 | 3/2004 | Chinn et al. | |
| 6,706,064 B1 * | 3/2004 | Anson | 623/1.25 |
| 6,719,789 B2 | 4/2004 | Cox | |
| 6,730,118 B2 | 5/2004 | Spenser et al. | |
| 6,730,377 B2 | 5/2004 | Wang | |
| 6,733,525 B2 | 5/2004 | Yang et al. | |
| 6,736,846 B2 | 5/2004 | Cox | |
| 6,741,523 B1 * | 5/2004 | Bommarito et al. | 368/327 |
| 6,752,828 B2 | 6/2004 | Thornton | |
| 6,758,855 B2 | 7/2004 | Fulton, III et al. | |
| 6,769,434 B2 | 8/2004 | Liddicoat et al. | |
| 6,786,925 B1 | 9/2004 | Schoon | |
| 6,790,229 B1 | 9/2004 | Berreklouw | |
| 6,792,979 B2 | 9/2004 | Konya et al. | |
| 6,797,002 B2 | 9/2004 | Spence | |
| 6,821,297 B2 | 11/2004 | Snyders | |
| 6,830,575 B2 | 12/2004 | Stenzel et al. | |
| 6,830,584 B1 | 12/2004 | Seguin | |
| 6,830,585 B1 | 12/2004 | Artof | |
| 6,846,325 B2 | 1/2005 | Liddicoat | |
| 6,866,650 B2 | 3/2005 | Stevens | |
| 6,872,223 B2 | 3/2005 | Roberts | |
| 6,875,231 B2 | 4/2005 | Anduiza et al. | |
| 6,883,522 B2 | 4/2005 | Spence et al. | |
| 6,887,266 B2 | 5/2005 | Williams et al. | |
| 6,890,330 B2 | 5/2005 | Streeter et al. | |
| 6,893,460 B2 | 5/2005 | Spenser et al. | |
| 6,896,690 B1 | 5/2005 | Lambrecht et al. | |
| 6,908,481 B2 | 6/2005 | Cribier | |
| 6,913,600 B2 | 7/2005 | Valley et al. | |
| 6,929,653 B2 | 8/2005 | Streeter | |
| 6,936,066 B2 | 8/2005 | Palmaz et al. | |
| 6,939,365 B1 | 9/2005 | Fogarty et al. | |
| 6,951,571 B1 | 10/2005 | Srivastava | |
| 6,986,742 B2 | 1/2006 | Hart et al. | |
| 6,989,027 B2 | 1/2006 | Allen et al. | |
| 6,991,649 B2 | 1/2006 | Sievers | |
| 7,018,401 B1 | 3/2006 | Hyodoh et al. | |
| 7,041,128 B2 | 5/2006 | McGuckin, Jr. et al. | |
| 7,044,966 B2 | 5/2006 | Svanidze et al. | |
| 7,048,014 B2 | 5/2006 | Hyodoh et al. | |
| 7,097,659 B2 | 8/2006 | Woolfson et al. | |
| 7,101,396 B2 | 9/2006 | Artof et al. | |
| 7,105,016 B2 | 9/2006 | Shiu et al. | |
| 7,115,141 B2 | 10/2006 | Menz et al. | |
| 7,147,663 B1 | 12/2006 | Berg et al. | |
| 7,153,324 B2 | 12/2006 | Case et al. | |
| 7,160,319 B2 | 1/2007 | Chouinard et al. | |
| 7,175,656 B2 | 2/2007 | Khairkhahan | |
| 7,186,265 B2 | 3/2007 | Sharkawy et al. | |
| 7,195,641 B2 | 3/2007 | Palmaz et al. | |
| 7,198,646 B2 | 4/2007 | Figulla et al. | |
| 7,201,761 B2 | 4/2007 | Woolfson et al. | |
| 7,201,772 B2 | 4/2007 | Schwammenthal et al. | |
| 7,252,682 B2 | 8/2007 | Seguin | |
| 7,300,457 B2 | 11/2007 | Palmaz | |
| 7,300,463 B2 | 11/2007 | Liddicoat | |
| 7,316,706 B2 | 1/2008 | Bloom et al. | |
| 7,329,278 B2 | 2/2008 | Seguin | |
| 7,335,218 B2 | 2/2008 | Wilson et al. | |
| 7,338,520 B2 | 3/2008 | Bailey et al. | |
| 7,374,571 B2 | 5/2008 | Pease et al. | |
| 7,381,218 B2 | 6/2008 | Shreck | |
| 7,384,411 B1 | 6/2008 | Condado | |
| 7,429,269 B2 | 9/2008 | Schwammenthal et al. | |
| 7,442,204 B2 | 10/2008 | Schwammenthal et al. | |

| | | |
|---|---|---|
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn et al. |
| 7,556,646 B2 | 7/2009 | Yang et al. |
| 2001/0003314 A1 | 5/2001 | Davison et al. |
| 2001/0010017 A1* | 7/2001 | Letac et al. ............... 623/2.11 |
| 2001/0011189 A1 | 8/2001 | Drasler et al. |
| 2001/0021872 A1* | 9/2001 | Bailey et al. ............... 623/1.24 |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0002401 A1* | 1/2002 | McGuckin et al. ......... 623/1.19 |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0035396 A1 | 3/2002 | Heath |
| 2002/0042650 A1 | 4/2002 | Vardi et al. |
| 2002/0058995 A1 | 5/2002 | Stevens |
| 2002/0072789 A1 | 6/2002 | Hackett et al. |
| 2002/0077696 A1 | 6/2002 | Zadno-Azizi et al. |
| 2002/0095209 A1 | 7/2002 | Zadno-Azizi et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123803 A1 | 9/2002 | Snyders |
| 2002/0133183 A1 | 9/2002 | Lentz et al. |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Bonhoeffer et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149476 A1 | 7/2003 | Damm et al. |
| 2003/0149475 A1 | 8/2003 | Hyodoh et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0199972 A1 | 10/2003 | Zadno-Azizi et al. |
| 2003/0212410 A1 | 11/2003 | Stenzel et al. |
| 2003/0212452 A1 | 11/2003 | Zadno-Azizi et al. |
| 2003/0212454 A1 | 11/2003 | Scott et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0093005 A1 | 5/2004 | Durcan |
| 2004/0093060 A1 | 5/2004 | Sequin et al. |
| 2004/0097788 A1 | 5/2004 | Mourles et al. |
| 2004/0098112 A1 | 5/2004 | DiMatteo et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Berheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143809 A1 | 6/2005 | Salahieh |
| 2005/0148997 A1 | 7/2005 | Valley et al. |
| 2005/0165477 A1 | 7/2005 | Anduiza et al. |
| 2005/0187616 A1 | 8/2005 | Realyvasquez |
| 2005/0203549 A1 | 9/2005 | Realyvasquez |
| 2005/0203605 A1 | 9/2005 | Dolan |

| | | | | | | |
|---|---|---|---|---|---|---|
| 2005/0203618 A1 | 9/2005 | Sharkawy | | 2007/0255396 A1 | 11/2007 | Douk et al. |
| 2005/0222674 A1 | 10/2005 | Paine | | 2007/0288000 A1 | 12/2007 | Bonan |
| 2005/0228495 A1 | 10/2005 | Macoviak | | 2008/0004696 A1 | 1/2008 | Vesely |
| 2005/0234546 A1 | 10/2005 | Nugent | | 2008/0009940 A1 | 1/2008 | Cribier |
| 2005/0240200 A1 | 10/2005 | Bergheim | | 2008/0015671 A1 | 1/2008 | Bonhoeffer |
| 2005/0240263 A1 | 10/2005 | Fogarty et al. | | 2008/0021552 A1 | 1/2008 | Gabbay |
| 2005/0261759 A1 | 11/2005 | Lambrecht et al. | | 2008/0048656 A1 | 2/2008 | Tan |
| 2005/0283962 A1 | 12/2005 | Boudjemline | | 2008/0065001 A1 | 3/2008 | Marchand et al. |
| 2006/0004439 A1 | 1/2006 | Spenser et al. | | 2008/0065206 A1 | 3/2008 | Liddicoat |
| 2006/0009841 A1 | 1/2006 | McGuckin et al. | | 2008/0071361 A1 | 3/2008 | Tuval et al. |
| 2006/0052867 A1 | 3/2006 | Revuelta et al. | | 2008/0071362 A1 | 3/2008 | Tuval et al. |
| 2006/0058775 A1 | 3/2006 | Stevens et al. | | 2008/0071363 A1 | 3/2008 | Tuval et al. |
| 2006/0089711 A1 | 4/2006 | Dolan | | 2008/0071366 A1 | 3/2008 | Tuval et al. |
| 2006/0100685 A1 | 5/2006 | Seguin et al. | | 2008/0071368 A1 | 3/2008 | Tuval et al. |
| 2006/0116757 A1 | 6/2006 | Lashinski et al. | | 2008/0077234 A1 | 3/2008 | Styrc |
| 2006/0135964 A1 | 6/2006 | Vesely | | 2008/0082165 A1 | 4/2008 | Wilson et al. |
| 2006/0142848 A1 | 6/2006 | Gabbay | | 2008/0082166 A1 | 4/2008 | Styrc et al. |
| 2006/0167474 A1 | 7/2006 | Bloom et al. | | 2008/0133003 A1 | 6/2008 | Seguin et al. |
| 2006/0178740 A1 | 8/2006 | Stacchino et al. | | 2008/0140189 A1 | 6/2008 | Nguyen et al. |
| 2006/0195134 A1 | 8/2006 | Crittenden | | 2008/0147105 A1 | 6/2008 | Wilson et al. |
| 2006/0206192 A1 | 9/2006 | Tower et al. | | 2008/0147180 A1 | 6/2008 | Ghione et al. |
| 2006/0206202 A1 | 9/2006 | Bonhoefer et al. | | 2008/0147181 A1 | 6/2008 | Ghione et al. |
| 2006/0247763 A1 | 11/2006 | Slater | | 2008/0147182 A1 | 6/2008 | Righini et al. |
| 2006/0259134 A1 | 11/2006 | Schwammenthal et al. | | 2008/0154356 A1 | 6/2008 | Obermiller et al. |
| 2006/0259136 A1 | 11/2006 | Nguyen et al. | | 2008/0161910 A1 | 7/2008 | Revuelta et al. |
| 2006/0259137 A1 | 11/2006 | Artof et al. | | 2008/0161911 A1 | 7/2008 | Revuelta et al. |
| 2006/0265056 A1 | 11/2006 | Nguyen et al. | | 2008/0183273 A1 | 7/2008 | Mesana et al. |
| 2006/0271166 A1 | 11/2006 | Thill et al. | | 2008/0188928 A1 | 8/2008 | Salahieh et al. |
| 2006/0271175 A1 | 11/2006 | Woolfson et al. | | 2008/0215143 A1 | 9/2008 | Seguin et al. |
| 2006/0276874 A1 | 12/2006 | Wilson et al. | | 2008/0215144 A1 | 9/2008 | Ryan et al. |
| 2006/0282161 A1 | 12/2006 | Huynh et al. | | 2008/0228254 A1 | 9/2008 | Ryan |
| 2007/0005129 A1 | 1/2007 | Damm et al. | | 2008/0228263 A1 | 9/2008 | Ryan |
| 2007/0005131 A1 | 1/2007 | Taylor | | 2008/0234797 A1 | 9/2008 | Styrc |
| 2007/0010878 A1 | 1/2007 | Raffiee et al. | | 2008/0243246 A1 | 10/2008 | Ryan et al. |
| 2007/0016286 A1 | 1/2007 | Case et al. | | 2008/0255651 A1 | 10/2008 | Dwork |
| 2007/0027518 A1 | 2/2007 | Herrmann et al. | | 2008/0255660 A1 | 10/2008 | Guyenot et al. |
| 2007/0027533 A1 | 2/2007 | Douk | | 2008/0255661 A1 | 10/2008 | Straubinger et al. |
| 2007/0043435 A1 | 2/2007 | Seguin et al. | | 2008/0262593 A1 | 10/2008 | Ryan et al. |
| 2007/0051377 A1 | 3/2007 | Douk et al. | | 2009/0005863 A1 | 1/2009 | Goetz et al. |
| 2007/0073392 A1 | 3/2007 | Heyninck-Janitz | | 2009/0012600 A1 | 1/2009 | Styrc et al. |
| 2007/0078509 A1 | 4/2007 | Lotfy et al. | | 2009/0048656 A1 | 2/2009 | Wen |
| 2007/0078510 A1 | 4/2007 | Ryan | | 2009/0054976 A1 | 2/2009 | Tuval et al. |
| 2007/0088431 A1 | 4/2007 | Bourang et al. | | 2009/0069886 A1 | 3/2009 | Suri et al. |
| 2007/0093869 A1 | 4/2007 | Bloom et al. | | 2009/0069887 A1 | 3/2009 | Righini et al. |
| 2007/0100439 A1 | 5/2007 | Cangialosi | | 2009/0069889 A1 | 3/2009 | Suri et al. |
| 2007/0100440 A1 | 5/2007 | Figulla | | 2009/0138079 A1 | 5/2009 | Tuval et al. |
| 2007/0100449 A1 | 5/2007 | O—Neil et al. | | 2009/0164004 A1 | 6/2009 | Cohn |
| 2007/0112415 A1 | 5/2007 | Bartlett | | 2009/0171447 A1 | 7/2009 | VonSegesser et al. |
| 2007/0162102 A1 | 7/2007 | Ryan et al. | | 2009/0192585 A1 | 7/2009 | Bloom et al. |
| 2007/0162113 A1 | 7/2007 | Sharkawy et al. | | 2009/0192586 A1 | 7/2009 | Tabor et al. |
| 2007/0185513 A1 | 8/2007 | Woolfson et al. | | 2009/0192591 A1 | 7/2009 | Ryan et al. |
| 2007/0203391 A1 | 8/2007 | Bloom et al. | | 2009/0198316 A1 | 8/2009 | Laske et al. |
| 2007/0225681 A1 | 9/2007 | House | | 2009/0216310 A1 | 8/2009 | Straubinger et al. |
| 2007/0232898 A1 | 10/2007 | Huynh et al. | | 2009/0216312 A1 | 8/2009 | Straubinger et al. |
| 2007/0233228 A1 | 10/2007 | Eberhardt et al. | | 2009/0216313 A1 | 8/2009 | Straubinger et al. |
| 2007/0233237 A1 | 10/2007 | Krivoruchko | | 2009/0240264 A1 | 9/2009 | Tuval et al. |
| 2007/0233238 A1 | 10/2007 | Huynh et al. | | 2009/0240320 A1 | 9/2009 | Tuval |
| 2007/0238979 A1 | 10/2007 | Huynh et al. | | | | |
| 2007/0239254 A1 | 10/2007 | Marchand et al. | | FOREIGN PATENT DOCUMENTS | | |
| 2007/0239265 A1 | 10/2007 | Birdsall | | | | |
| 2007/0239266 A1 | 10/2007 | Birdsall | | EP | 1057459 A1 | 6/2000 |
| 2007/0239269 A1 | 10/2007 | Dolan et al. | | EP | 1255510 | 11/2002 |
| 2007/0239273 A1 | 10/2007 | Allen | | EP | 0937439 B1 | 9/2003 |
| 2007/0244544 A1 | 10/2007 | Birdsall et al. | | EP | 1340473 | 9/2003 |
| 2007/0244545 A1 | 10/2007 | Birdsall et al. | | EP | 0819013 | 6/2004 |
| 2007/0244546 A1 | 10/2007 | Francis | | GB | 2433700 | 12/2007 |
| 2007/0244553 A1 | 10/2007 | Rafiee et al. | | WO | 95/29640 | 11/1995 |
| 2007/0244554 A1 | 10/2007 | Rafiee et al. | | WO | 98/14137 | 4/1998 |
| 2007/0244555 A1 | 10/2007 | Rafiee et al. | | WO | 00/44313 | 8/2000 |
| 2007/0244556 A1 | 10/2007 | Rafiee et al. | | WO | 00/47136 | 8/2000 |
| 2007/0244557 A1 | 10/2007 | Rafiee et al. | | WO | 01/35870 | 5/2001 |
| 2007/0250160 A1 | 10/2007 | Rafiee | | WO | 02/36048 | 5/2002 |
| 2007/0255394 A1 | 11/2007 | Ryan | | WO | 03/003943 | 1/2003 |

| | | |
|---|---|---|
| WO | 03/003949 | 1/2003 |
| WO | 03/011195 | 2/2003 |
| WO | 03/030776 | 4/2003 |
| WO | 2004/019811 | 3/2004 |
| WO | 2004/019825 | 3/2004 |
| WO | 2004/023980 | 3/2004 |
| WO | 2004/041126 | 5/2004 |
| WO | 2004/058106 | 7/2004 |
| WO | 2004/089250 | 10/2004 |
| WO | 2004/089253 | 10/2004 |
| WO | 2005/004753 | 1/2005 |
| WO | 2005/009285 | 2/2005 |
| WO | 2005/027790 | 3/2005 |
| WO | 2005/046528 | 5/2005 |
| WO | 2008/047354 | 4/2008 |
| WO | 2008/100599 | 8/2008 |
| WO | 2008/150529 | 12/2008 |
| WO | 2009/002548 | 12/2008 |
| WO | 2009/029199 | 3/2009 |
| WO | 2009/042196 | 4/2009 |
| WO | 2009/045338 | 4/2009 |
| WO | 2009/061389 | 5/2009 |
| WO | 2009/091509 | 7/2009 |

OTHER PUBLICATIONS

US Patent Application Publication 2001/0,007,956—Letac et al. (Published Jul. 12, 2001).
US Patent Application Publication 2001/0,010,017—Letac et al. (Published Jul. 26, 2001).
US Patent Application Publication 2001/0,021,872—Bailey et al. (Published Sep. 13, 2001).
US Patent Application Publication 2002/0,032,481—Gabbay (Published Mar. 14, 2002).
US Patent Application Publication 2002/0,042,651—Liddicoat (Published Apr. 11, 2002).
US Patent Application Publication 2002/0,107,565—Greenhalgh (Published Aug. 8, 2002).
US Patent Application Publication 2002/0,138,138—Yang (Published Sep. 26, 2002).
U.S. Appl. No. 12/050,184, filed Mar. 18, 2008.
U.S. Appl. No. 12/250,163, filed Oct. 13, 2008.
U.S. Appl. No. 61/192,199, filed Sep. 15, 2008.
U.S. Appl. No. 12/253,858, filed Oct. 17, 2008.
U.S. Appl. No. 12/596,343, filed Apr. 14, 2008.
U.S. Appl. No. 61/129,170, filed Jun. 9, 2008.
Andersen, H.R. et al, "Transluminal implantation of artificial heart valves. Description of a new expandable aortic valve and initial results with implantation by catheter technique in closed chest pigs." Euro. Heart J. (1992) 13:704-708.
Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.
Bailey, "Percutaneous Expandable Prosthetic Valves," In: Topol EJ, ed. Textbook of Interventional Cardiology. vol. II. Second edition. WB Saunders, Philadelphia, 1994:1268-1276.
Block, et al., "Percutaneous Approaches to Valvular Heart Disease," Current Cardiology Reports, vol. 7 (2005) pp. 108-113.
Bonhoeffer, et al, "Percutaneous Insertion of the Pulmonary Valve," Journal of the American College of Cardiology (United States), May 15, 2002, pp. 1664-1669.
Bonhoeffer, et al, "Percutaneous Mitral Valve Dilatation with the Multi-Track System," Catheterization and Cardiovascular Interventions — Official Journal of the Society for Cardiac Angiography & Interventions (United States), Oct. 1999, pp. 178-183.
Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.
Bonhoeffer, et al, "Technique and Results of Percutaneous Mitral Valvuloplasty With the Multi-Track System," Journal of Interventional Cardiology (United States), 200, pp. 263-268.

Bonhoeffer, et al, "Transcatheter Implantation of a Bovine Valve in Pulmonary Position: A Lamb Study," Circulation (United States), Aug. 15, 2000, pp. 813-816.
Boudjemline, et al, "Images in Cardiovascular Medicine. Percutaneous Aortic Valve Replacement in Animals," Circulation (United States), Mar. 16, 2004, 109, p. e161.
Boudjemline, et al, "Is Percutaneous Implantation of a Bovine Venous Valve in the Inferior Vena Cava a Reliable Technique to Treat Chronic Venous Insufficiency Syndrome?" Medical Science Monitor —International Medical Journal of Experimental and Clinical Research (Poland), Mar. 2004, pp. BR61-BR66.
Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.
Boudjemline, et al, "Percutaneous Aortic Valve Replacement: Will We Get There?" Heart (British Cardiac Society) (England), Dec. 2001, pp. 705-706.
Boudjemline, et al, "Percutaneous Closure of a Paravalvular Mitral Regurgitation with Amplatzer and Coil Prostheses," Archives des Maladies du Coeur Et Des Vaisseaux (France), May 2002, pp. 483-486.
Boudjemline, et al, "Percutaneous Implantation of a Biological Valve in the Aorta to Treat Aortic Valve Insufficiency—A Sheep Study," Medical Science Monitor —International Medical Journal of Experimental and Clinical Research (Poland), Apr. 2002, pp. Br113-Br116.
Boudjemline, et al, "Percutaneous Implantation of a Biological Valve in Aortic Position: Preliminary Results in a Sheep Study" European Heart Journal 22, Sep. 2001, p. 630.
Boudjemline, et al, "Percutaneous Implantation of a Valve in the Descending Aorta in Lambs," European Heart Journal (England), Jul. 2002, pp. 1045-1049.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline, et al, "Percutaneous Valve Insertion: A New Approach," Journal of Thoracic and Cardiovascular Surgery (United States), Mar. 2003, pp. 741-742.
Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.
Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology (Ireland), 2001, pp. 89-93.
Boudjemline, et al, "Transcatheter Reconstruction of the Right Heart," Cardiology in the Young (England), Jun. 2003, pp. 308-311.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Hanzel, et al., "Complications of percutaneous aortic valve replacement: experience with the Criber-Edwards™ percutaneous heart valve," EuroIntervention Supplements (2006), 1 (Supplement A) A3-A8.
Huber, et al., "Do Valved Stents Compromise Coronary Flow?" Eur. J. Cardiothorac. Surg. 2004;25:754-759.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.

Khambadkone, et al, "Percutaneous Pulmonary Valve Implantation: Early and Medium Term Results," Circulation 108 (17 Supplement), Oct. 28, 2003, p. IV-375.

Khambadkone, et al, "Percutaneous Pulmonary Valve Implantation: Impact of Morphology on Case Selection," Circulation 108 (17 Supplement), Oct. 28, 2003, p. IV-642-IV-643.

Lutter, et al, "Percutaneous Aortic Valve Replacement: An Experimental Study. I. Studies on Implantation," The Journal of Thoracic and Cardiovascular Surgery, Apr. 2002, pp. 768-776.

Lutter, et al, "Percutaneous Valve Replacement: Current State and Future Prospects," Annals of Thoracic Surgery (Netherlands), Dec. 2004, pp. 2199-2206.

Medtech Insight, "New Frontiers in Heart Valve Disease," vol. 7, No. 8 (2005).

Palacios, "Percutaneous Valve Replacement and Repair, Fiction or Reality?" Journal of American College of Cardiology, vol. 44, No. 8 (2004) pp. 1662-1663.

Ruiz, "Transcathether Aortic Valve Implantation and Mitral Valve Repair: State of the Art," Pediatric Cardiology, vol. 26, No. 3 (2005).

Saliba, et al, "Treatment of Obstructions of Prosthetic Conduits by Percutaneous Implantation of Stents," Archives des Maldies du Coeur et des Vaisseaux (France), 1999, pp. 591-596.

Webb, et al., "Percutaneous Aortic Valve Implantation Retrograde from the Femoral Artery," Circulation (2006), 113;842-850.

Yonga, et al, "Effect of Percutaneous Balloon Mitral Valvotomy on Pulmonary Venous Flow in Severe Mitral Stenosis," East African Medical Journal (Kenya), Jan. 1999, pp. 28-30.

Yonga, et al, "Percutaneous Balloon Mitral Valvotomy: Initial Experience in Nairobi Using a New Multi-Track Catheter System," East African Medical Journal (Kenya), Feb. 1999, pp. 71-74.

Yonga, et al, "Percutaneous Transluminal Balloon Valvuloplasty for Pulmonary Valve Stenosis: Report on Six Cases," East African Medical Journal (Kenya), Apr. 1994, pp. 232-235.

Yonga, et al, "Percutaneous Transvenous Mitral Commissurotomy in Juvenile Mitral Stenosis," East African Medical Journal (Kenya), Apr. 2003, pp. 172-174.

Commeau et al, "Percutaneous balloon dilatation of calcific aortic valve stenosis: anatomical and haemodynamic evaluation," 1988, British Heart Journal, 59:227-238.

Stassano et al., "Mid-term results of the valve-on-valve technique for bioprosthetic failure," Eur. J. Cardiothorac. Surg. 2000; 18:453-457.

Expert report of Dr. Nigel Buller, dated Jan. 12, 2009, Edwards' United Kingdom action for invalidity, Claim No. HC 08CO0934.

Expert report of Dr. Nigel Buller, non-confidential annex—infringement, dated Jan. 12, 2009, Edwards' United Kingdom action for invalidity, Claim No. HC 08CO0934.

Expert report of Dr. Rodolfo Quijano, dated Jan. 9, 2009, Edwards' United Kingdom action for invalidity, Claim No. HC 08CO0934.

First Expert report of Prof. David Williams, dated Jan. 12, 2009, Edwards' United Kingdom action for invalidity, Claim No. HC 08CO0934.

First Expert report of Prof. Martin Rothman, dated Jan. 12, 2009, Edwards' United Kingdom action for invalidity, Claim No. HC 08CO0934.

Fourth Expert report of Prof. Martin Rothman, dated Apr. 22, 2009, Edwards' United Kingdom action for invalidity, Claim No. HC 08CO0934.

Second Expert report of Dr. Nigel Buller, dated Feb. 25, 2009, Edwards' United Kingdom action for invalidity, Claim No. HC 08CO0934.

Second Expert report of Dr. Rodolfo Quijano, dated Feb. 26, 2009, Edwards' United Kingdom action for invalidity, Claim No. HC 08CO0934.

Second Expert report of Prof. David Williams, dated Feb. 5, 2009, Edwards' United Kingdom action for invalidity, Claim No. HC 08CO0934.

Second Expert report of Prof. Martin Rothman, dated Feb. 5, 2009, Edwards' United Kingdom action for invalidity, Claim No. HC 08CO0934.

Third Expert report of Dr. Nigel Buller, dated Apr. 21, 2009, Edwards' United Kingdom action for invalidity, Claim No. HC 08CO0934.

Third Expert report of Dr. Rudolfo Quijano, dated Apr. 27, 2009, Edwards' United Kingdom action for invalidity, Claim No. HC 08CO0934.

Third Expert report of Prof. David Williams, dated Apr. 22, 2009, Edwards' United Kingdom action for invalidity, Claim No. HC 08CO0934.

Pavcnik et al., "Aortic and venous valve for percutaneous insertion," Min. Invas. Ther. & Allied Techol. 2000, vol. 9, pp. 287-292.

First Expert report of Dr. Nigel Person Buller (30 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.

Second Expert report of Dr. Nigel Person Buller (5 pages), *Corevalve, Inc.* v. *Edwards Lifesciences AG and Edwards Lifesciences PVT, Inc.*, High Court of Justice—Chancery Division Patents Court, United Kingdom, HC-07-C01243.

Drawing by Dr. Buller (Edwards Expert) of his interpretation of the "higher stent" referred to at col. 8, lines 13-222 of Andersen EP 592410B1 (1 page), *Corevalve, Inc.*v. *Edwards Lifesciences AG and Edwards Lifesciences PVT, Inc.*, High Court of Justice—Chancery Division Patents Court, United Kingdom, Case No. HC-07-C01243.

Drawing by Dr. Buller (Edwards Expert) of "higher stent" on the schematic representation of the aortic valve area set out in Figure 2 of Rothman's first expert report (1 page), *Corevalve, Inc.* v. *Edwards Lifesciences AG and Edwards Lifesciences PVT, Inc.*, High Court of Justice—Chancery Division Patents Court, United Kingdom, Case No. HC-07-C01243.

First Expert report of Professor John R. Pepper (20 pages), *Corevalve, Inc.* v. *Edwards Ltfesciences AG and Edwards Lifesciences PVT, Inc.*, High Court of Justice—Chancery Division Patents Court, United Kingdom, Case No. HC-07-C01243.

Second Expert report of Professor John R. Pepper (3 pages), *Corevalve, Inc.* v. *Edwards Lifesciences AG and Edwards Ltfesciences PVT, Inc.*, High Court of Justice—Chancery Division Patents Court, United Kingdom, Case No. HC-07C01243.

First Expert report of Dr. Anthony C. Lunn (7 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.

First Witness statement of Stanton Rowe (9 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.

Second Witness statement of Stanton Rowe (3 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.

PVT slides naming Alain Cribier, Martin Leon, Stan Rabinovich and Stanton Rowe (16 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.

First Expert report of Professor Martin Terry Rothman (75 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.

Reply Expert report of Professor Martin Terry Rothman (9 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.

First Expert report of Richard A. Hillstead (41 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.

Reply Expert report of Richard A. Hillstead (9 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.

\* cited by examiner

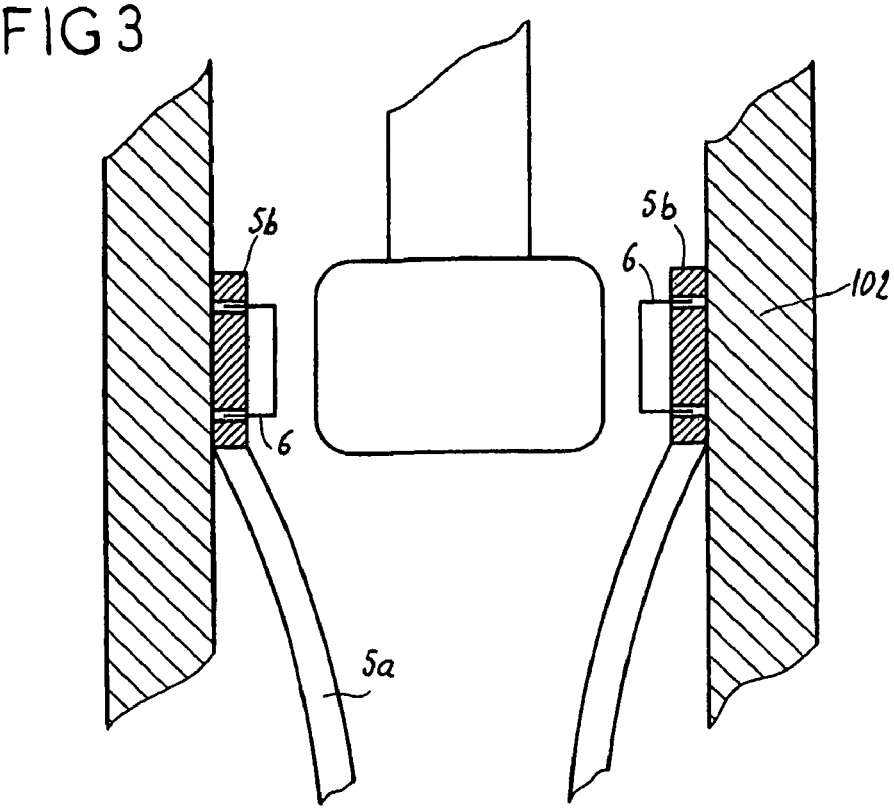
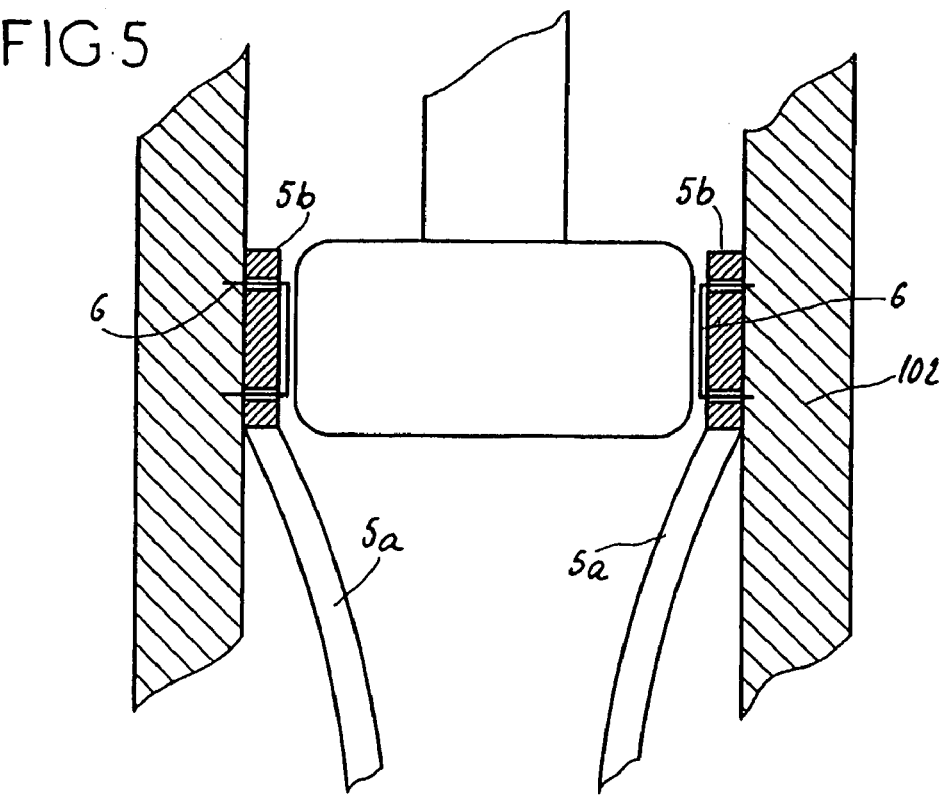

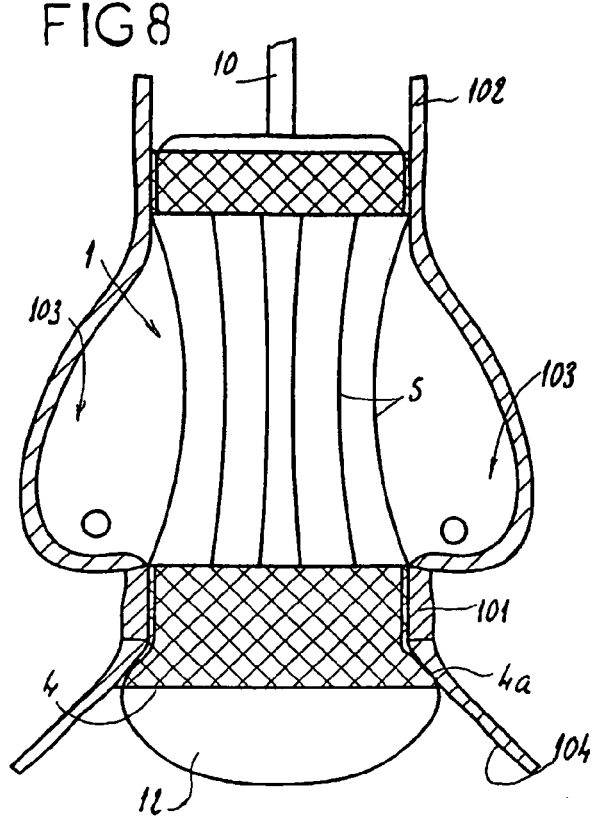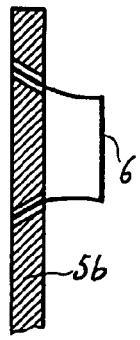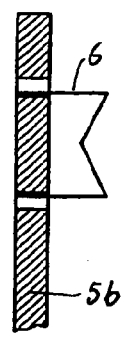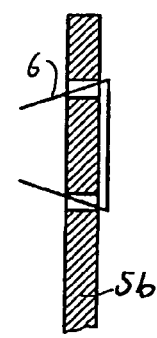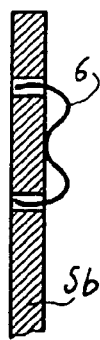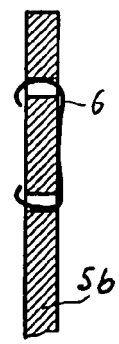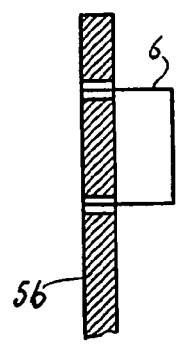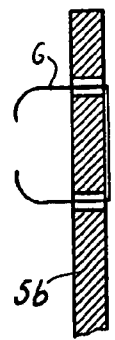

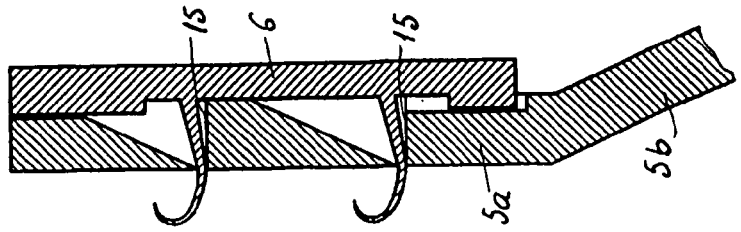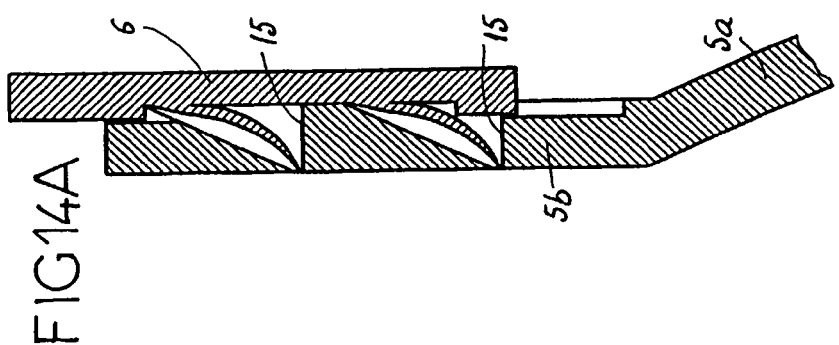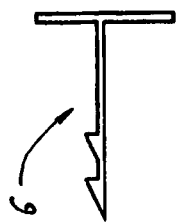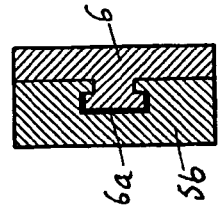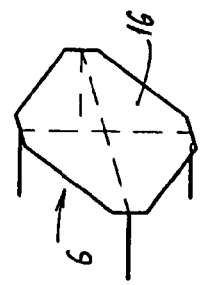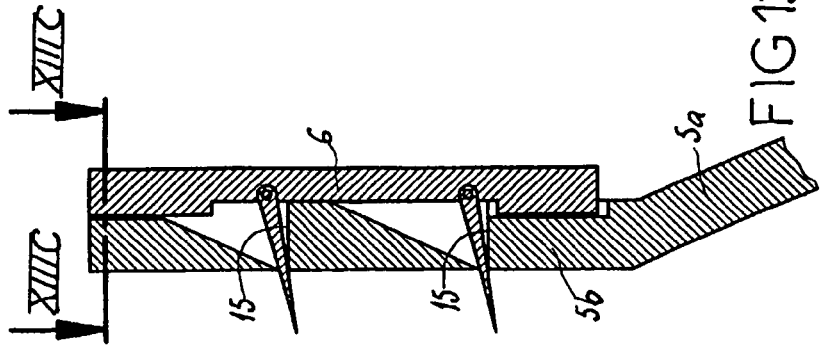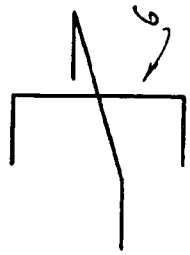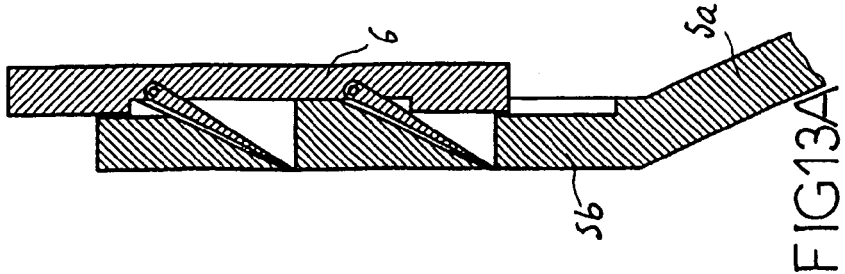

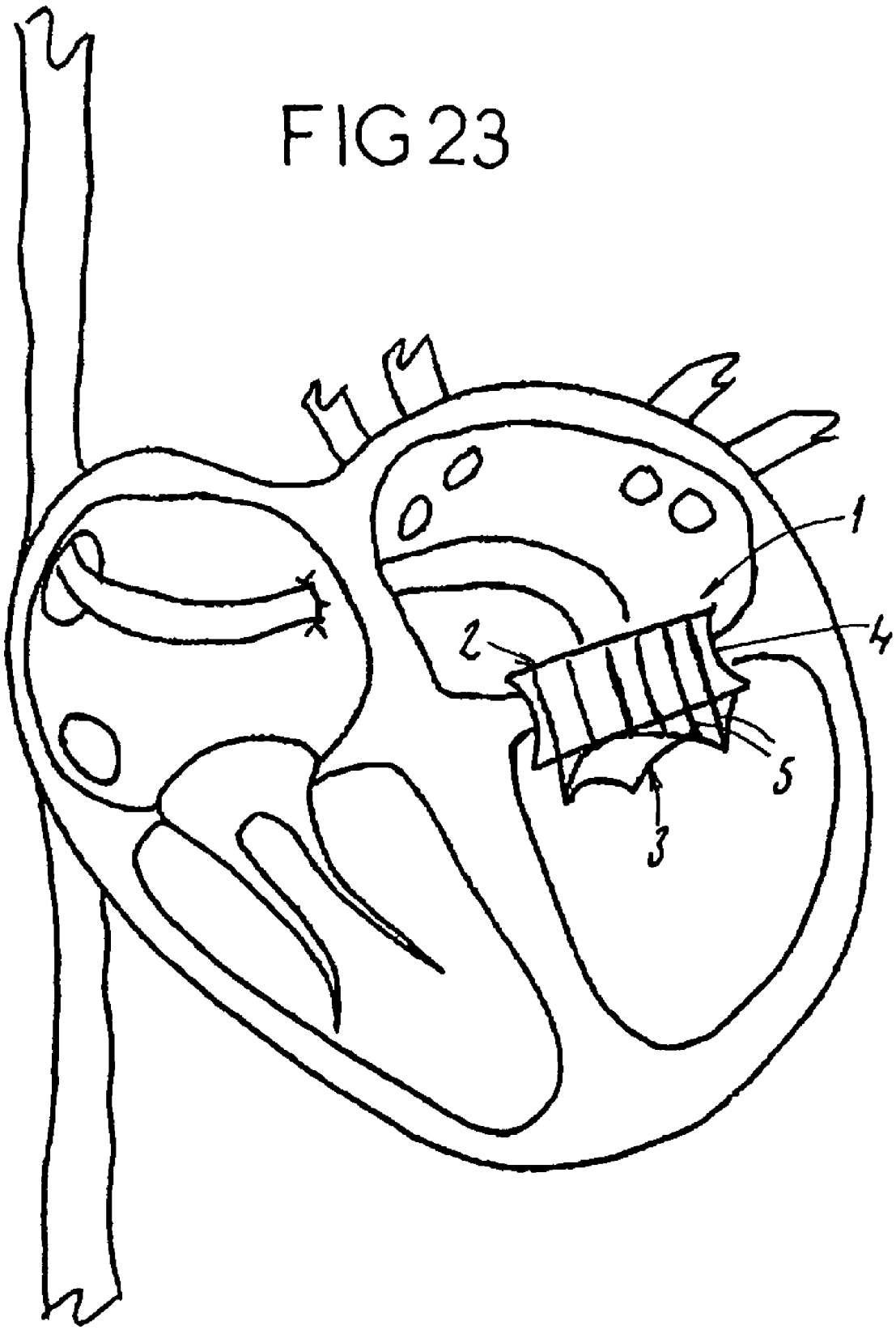

US 7,682,390 B2

ASSEMBLY FOR SETTING A VALVE PROSTHESIS IN A CORPOREAL DUCT

CROSS-REFERENCE TO RELATED APPLICATIONS

The present application is the U.S. national phase under §371 of International Application No. PCT/FR02/02745, filed on Jul. 31, 2002, which was published in a language other than English and which claimed priority from French Application No. 01/10281, filed on Jul. 30, 2001.

BACKGROUND OF THE INVENTION

1. Field of the Invention

The present invention relates to an assembly for setting a valve prosthesis in a corporeal duct, especially a cardiac valve and in particular an aortic valve.

2. Description of the Related Art

Documents WO 91/17720, WO 98/29057 and EP 1 057 460 each describe an assembly of this type, comprising the valve prosthesis to implant; a radially expandable reinforcement, called a "stent," clean, in the expanded state, to bear against the wall of the target corporeal duct, this bearing allowing this stent to be immobilized with respect to this wall; and means for fixing the valve to the stent. Setting of the stent thus allows the valve to be installed in the corporeal duct, eliminating the necessity for outside access and thus for direct surgical intervention.

However, this technique may have important disadvantages leading to a risk of damage to the valve by the balloon utilized for expanding the stent, and limiting the expansion force that it is possible to give to the stent. This limitation has an effect on the anchoring of the stent, making a displacement of the assembly possible. This limitation also has an effect on the sealing of the stent at the valvular ring, which is particularly affected when the calcified areas give the valvular ring an irregular form and/or a certain rigidity. Expansion of the balloon may also lead to damage to the corporeal duct, particularly when the duct is in a blood vessel.

Furthermore, the target corporeal duct may not present a perfectly circular cross section at the implantation site, particularly when the natural valve is retained and when this valve, or valvular ring, comprises calcified areas. Whatever the degree of expansion of the stent, the circular shape of this stent then may not be suitable for the specific anatomy of the implantation site. A defect in sealing of the implanted valve may then result. Furthermore, the stent presents a certain rigidity, which leads to a rigidity in the implantation catheter. This rigidity may make the advancement of this catheter to the implantation site difficult.

Another disadvantage of the prior technique is the direct connection of the leaflets' commissures to the stent. A different than anticipated expansion of the stent, and thus of the valve, results, which may lead to a poor coaptation of the leaflets and thus a defective operation of the valve. The stent must consequently be subjected to a predetermined expansion that prevents, or makes difficult, the adaptation of this stent to the anatomic variability. The prior technique also has the disadvantage of, in cases of aortic valve implantation, inducing a risk of obstruction of the coronary ostia.

SUMMARY OF THE INVENTION

The present invention aims to remedy one or more of these disadvantages. The assembly that the invention relates to comprises a the valve prosthesis to implant and a valve support, the valve and the support being shaped so that they are able to adopt a position of radial contraction, which allows their insertion into the target corporeal duct with the help of insertion/extension means, and a radial extension position, in which the support is immobilized with respect to the wall of the target corporeal duct.

According to the invention, the support comprises at least one tubular portion in a pliable material that is slightly stretchable in the circumferential direction, which presents, in its extension position, a dimension in the circumferential direction substantially corresponding to the dimension in the circumferential direction of the location of the corporeal duct in regards to which this tubular portion must be implanted. The invention further comprises means for fixating this tubular portion to the wall of the corporeal duct, and a plurality of elongated reinforcing elements, arranged on the circumference of said tubular portion and linked to said tubular portion independently of one another, the valve being linked at least partially to these elongated reinforcing elements, in particular at the commissures of its leaflets. The elongated reinforcing elements jointly form, in extended position, a structure having a predetermined diameter that ensures sufficient extension of said valve.

The support according to the invention thus is not formed by an expandable stent bearing by friction against the wall of the target corporeal duct but is formed by (i) at least one pliable tubular portion that is slightly stretchable in the circumference, fitted with fixation means at the wall of the corporeal duct, and (ii) an installation structure for the valve, extended by such tubular portion or portions. The latter are only subjected to active extension, achieved in particular by means of one or more inflatable balloons, at the areas equipped with the fixation means; the leaflets of the valve are linked to the elongated reinforcing elements and are thus placed on a portion of the support that does not have to be stimulated by the extension means, so that the risk of deterioration of these leaflets by these extension means is eliminated.

The extension of the tubular portion or portions does not require a radial force as great as that necessary for extending a stent, and the slight stretchability of the tubular portions beyond their extension position allows the risk of deterioration of the corporeal duct resulting from the utilization of the inflatable balloons to be eliminated. The pliable structure of the tubular portion or portions furthermore allows them to be perfectly adapted to the specific anatomy of the implantation site, particularly when the site is not circular in its cross section due to the presence of calcified areas. The support has an overall longitudinal rigidity definitely less than that of a stent, which significantly facilitates the advancement of the implantation catheter to the implantation site.

The valve may be constructed of a biological tissue or of a synthetic material such as, for example, a polymer. The valve may present a base ring allowing its tight connection, particularly by sutures, to the tubular portion or to one of the tubular portions. The commissures of the leaflets are not linked to an expandable area, and the structure formed by the elongated reinforcing elements assures the sufficient extension of these leaflets. The tubular portion, or a peripheral wall that comprises the valve, may present side openings to allow the blood to flow naturally to the coronary ostia, without risk of stagnation.

Preferably, the tubular portion or portions present at least one inflatable peripheral chamber, which may be inflated so that a joint is formed which ensures the sealing between this tubular portion and the wall of the target corporeal duct. The proximal area of the tubular portion, or of the proximal tubular portion in case of a plurality of tubular portions, may present a truncated cone shape suitable for bearing against the wall of the ventricle. The tubular portion or portions may be constituted of a biological or synthetic material, particularly a polymer or a fiber fabric known under the name "dacron."

The fixation means are preferably constituted of anchoring fasteners presenting anchoring prongs. These anchoring prongs are configured to be inserted into the wall of the target corporeal duct at the end of the extension of the tubular portions. These fasteners may be plastically deformed; the means may then be provided for extending the anchoring prongs of these fasteners non-radially, particularly in an oblique orientation or according to a trajectory curve, in order to reinforce the resistance of the anchoring obtained.

At least one of these fasteners may be in a shape-retaining material such as the nickel and titanium alloy known under the name "NITINOL." Such a fastener is preferably configured to adopt before implantation an insertion configuration, in which its anchoring prongs are substantially radially positioned with respect to the tubular portion so that they can be inserted in the wall of the duct, and an anchoring configuration, in which these same anchoring prongs are positioned non-radially and/or are curved in order to ensure the anchoring of the fasteners in the wall of the target corporeal duct.

The fixation means may also comprise a biological glue, which may be contained in breakable blisters placed on the radial external surface of the tubular portion or portions. These blisters break when they are crushed between the tubular portion or portions and the wall of the corporeal duct, thus freeing the glue.

Each elongated reinforcing element advantageously presents a curved form and is placed with its convex side radially turned toward the inside of the support, so that this support presents, at its median zone, a smaller diameter compared to the diameter that it presents at its axial extremities. This smaller diameter allows any risk of covering the coronary ostia to be eliminated.

In an alternative embodiment of the invention, the support comprises two tubular portions, such as that described above, whereby one of the extremities of the elongated reinforcing elements is linked to one of these tubular portions while the other extremity of these elongated reinforcing elements is linked to the other tubular portion. The extension of these two tubular portions ensures a perfect extension of the elongated reinforcing elements.

According to another possible embodiment of the invention, the support comprises a single tubular portion extending on the support assembly, to the wall of which are linked the elongated reinforcing elements. This single tubular portion may present the aforementioned side openings with regard to the coronary ostia.

According to still another possible embodiment of the invention, the support comprises a single tubular portion, from which the elongated reinforcing elements protrude, on an axial extremity of this tubular portion. This support may in particular allow the implantation of a mitral valve.

To be well understood, the invention is again described below with reference to the attached schematic drawing representing, by way of non-limiting indication, a preferred form of embodiment of the assembly, to which the invention relates.

BRIEF DESCRIPTION OF THE DRAWINGS

FIG. 3 is a partial schematic view of a portion of the assembly of FIG. 1 prior to anchoring to an intralumenal wall;

FIG. 5 is a partial schematic view of a portion of the assembly of FIG. 3 after anchoring to an intralumenal wall;

FIG. 8 is a schematic view of yet another alternative embodiment of the present valve assembly;

FIGS. 9A, 10A, 11A, 12A, 13A and 14A are schematic cross-sectional views of a portion of the assembly with varying embodiments of fastener before the fastener is placed in the anchoring position;

FIGS. 9B, 10B, 11B, 12B, 13B and 14B are views corresponding respectively to the FIGS. 9A, 10A, 11A, 12A, 13A and 14A, after the fastener is in the anchoring position;

FIG. 13C is a cross sectional view of the assembly of FIG. 13B taken across line XIIIC-XIIIC;

FIG. 15 is a schematic perspective view of another embodiment of a fastener;

FIG. 16 a schematic perspective view of yet another embodiment of a fastener;

FIG. 17 a schematic perspective view of yet another embodiment of a fastener;

FIG. 23 is a schematic view of one embodiment of the present inventive assembly shown applied to the mitral valve.

DETAILED DESCRIPTION OF THE PREFERRED EMBODIMENT

Figures 1, 2:
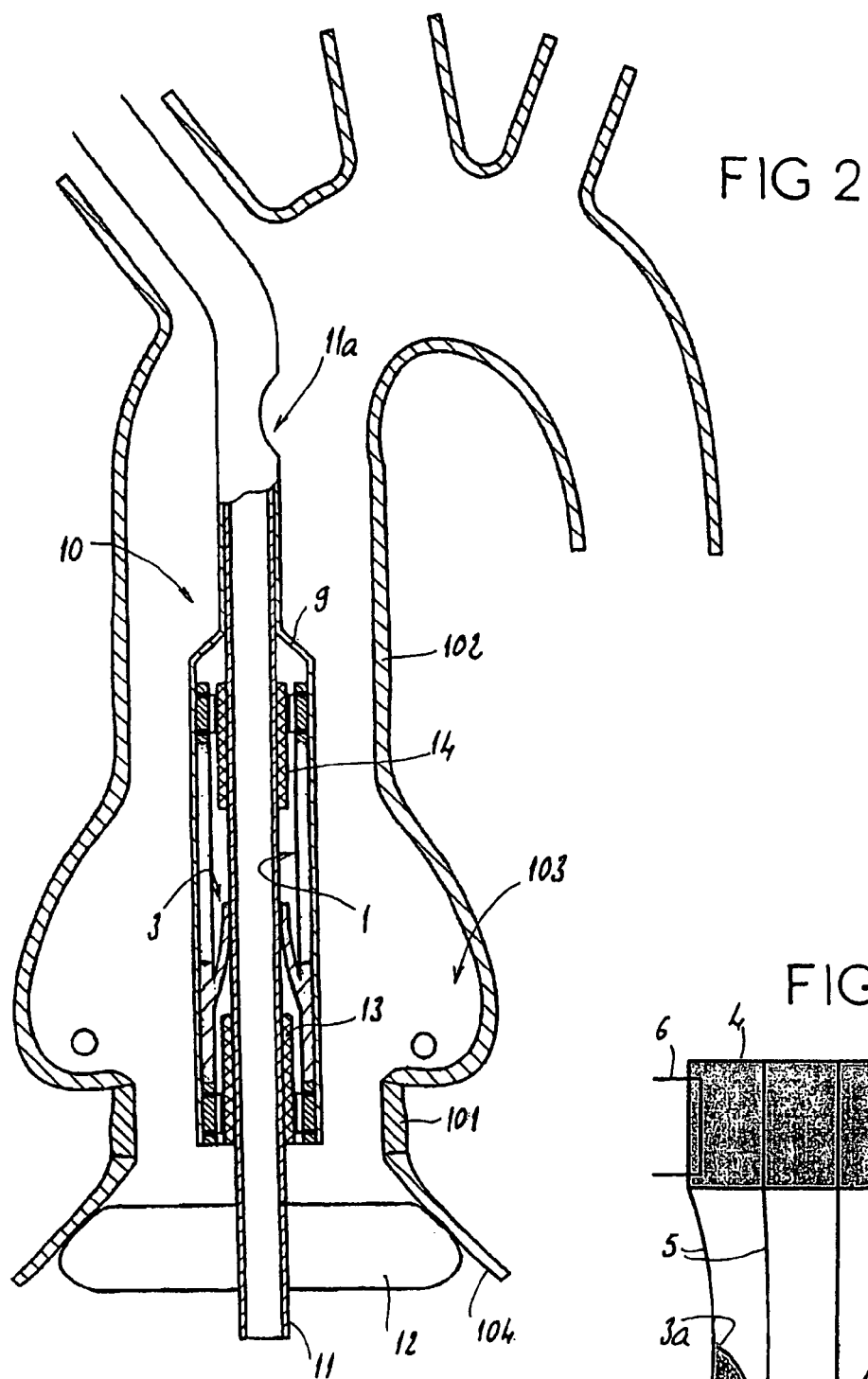
FIG. 1 is a schematic view of one embodiment of the present inventive prosthetic valve assembly.
FIG. 2 is a schematic cross-sectional view of the valve assembly of FIG. 1 shown in a delivered but not deployed state.
Figure 4:
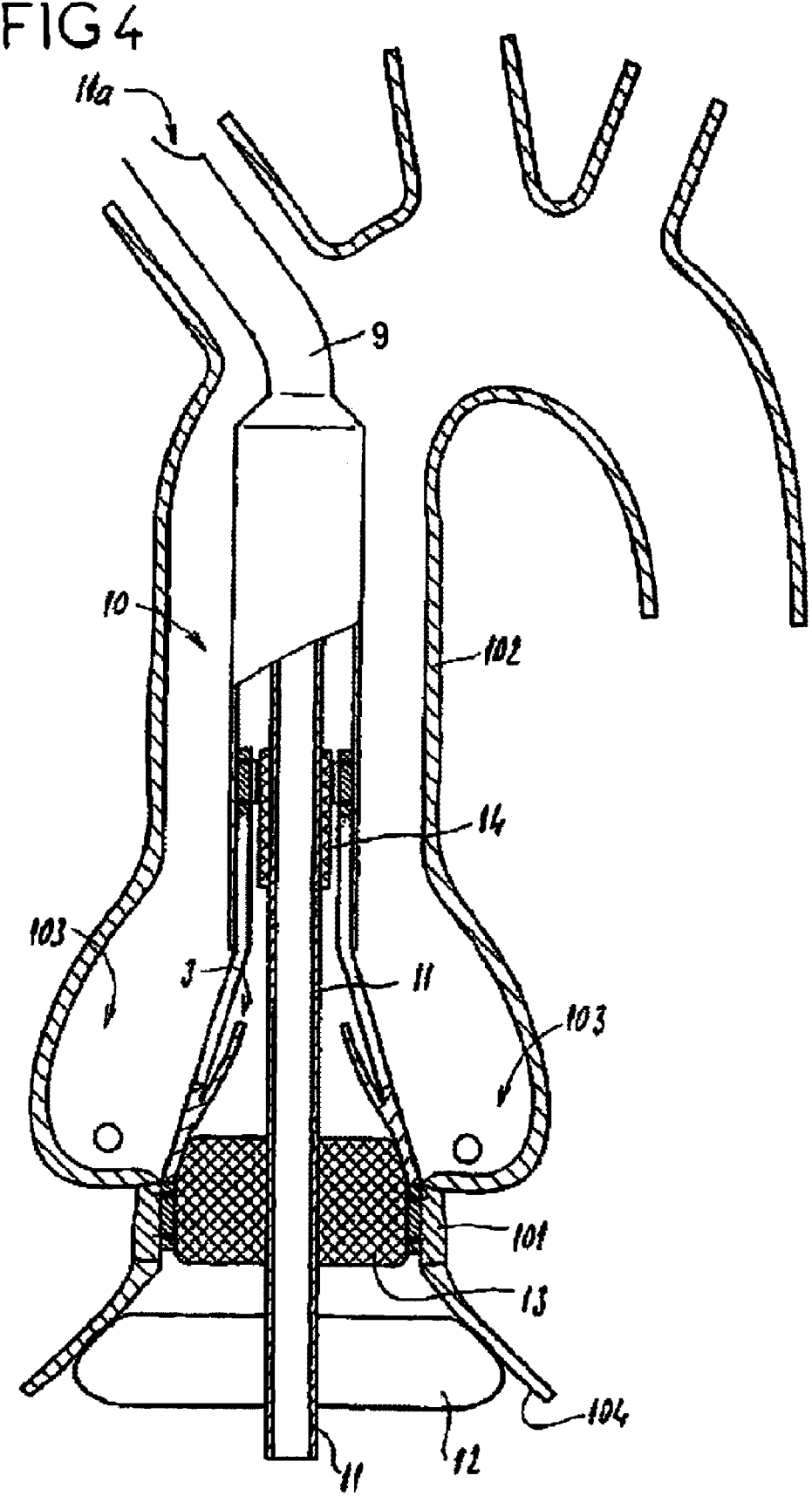
FIG. 4 is a schematic cross-sectional view of the present inventive prosthetic valve assembly of FIG. 2 shown in a partially deployed state.

Referring to FIG. 1, the present invention comprises a prosthetic valve assembly 1. The assembly 1 comprises a support 2 on which is mounted a valve prosthesis 3, which in one embodiment is an aortic valve. The support 2 preferably comprises a distal and proximal tubular portion 4 separated by a plurality of elongated reinforcing elements 5. The tubular portions 4 are preferably made of a pliable material that is slightly stretchable in the circumferential direction of these tubular portions 4. In particular, the tubular portions may be constructed of a polymer or of a fiber fabric known under the name "dacron," or even in a biological tissue like the pericardium. The diameter of these tubular portions 4 should preferably correspond to the diameter of the target native lumen, for example, the aorta, as shown in FIGS. 2 and 4, where the native valve ring 101, the wall 102 of the aorta, and the coronary ostia 103, are shown.

Each elongated reinforcing element 5 is constructed of a relatively rigid material, particularly of a metallic material. The element presents a preferably elongated curve portion 5a and two pallets 5b at distal and proximal ends, wherein the pallets provide a means to link the reinforcing elements to the respective tubular portions 4. As shown in FIG. 1, these elements 5 are regularly distributed on the periphery of the tubular portions 4 and are placed with their convex side turned radially toward the inside of the support 2. The latter thus presents, at its median zone, a smaller diameter than that which it presents at its axial extremities. Other configurations are contemplated for the reinforcing elements.

Figure 6:
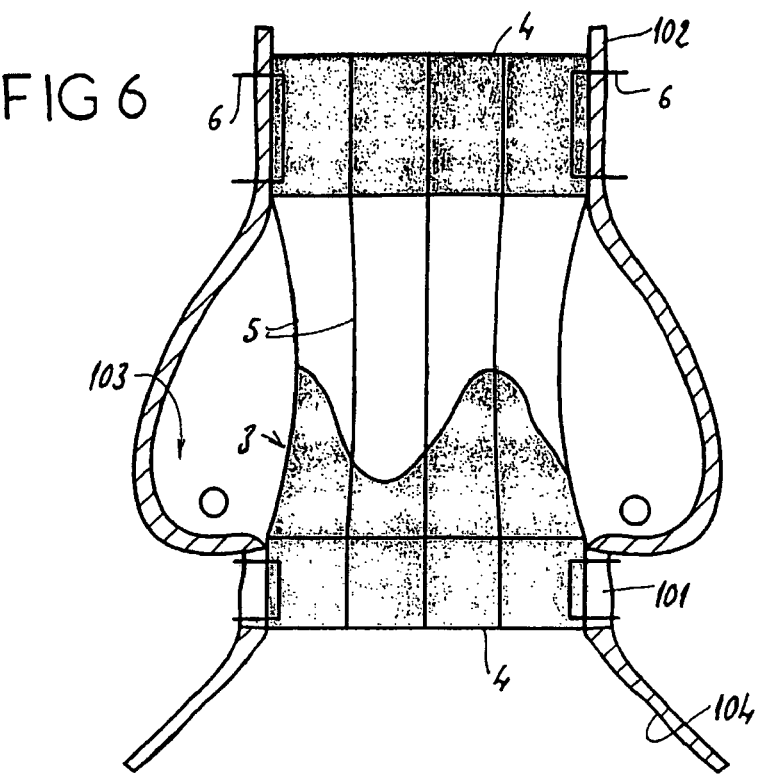
FIG. 6 is a schematic view of the assembly of FIG. 1 shown implanted.

Each pallet 5b is integrated to the corresponding tubular portion 4 and is fixed to the latter preferably by sutures, although other means are possible. The pallets further comprise a plurality of radially spaced holes in axial pairs of at least two through which pairs the side anchoring prongs of fasteners 6 may project. As shown in FIGS. 1 and 3, these side prongs are recessed, before implantation, in the radially spaced holes so that the fasteners 6 do not protrude outside of the outer radial surface of the tubular portion 4. These holes are preferably sized to retain the fasteners 6 by friction. The prongs of the fasteners 6 are preferably moved into an anchoring position, as shown in FIGS. 5 and 6, when an inflatable balloon or other means pushes the fasteners 6 from the interior of the prosthesis assembly 1.

The valve 3 is not in itself part of the present invention and is, thus, not described in great detail. The valve may be constructed of a biological tissue or of a synthetic material, particularly a polymer, and presents a base ring linked to a proximal tubular portion 4 particularly by suturing and leaflets whose commissures 3a are linked to the adjacent portions 5a of the elements 5. The connection of the base ring to the proximal portion 4 ensures the sealing of the valve 3 between this ring and this tubular portion, and the connection of the commissures 3a to the elements 5 allows the extension of the leaflets when the extension of the support 2 is achieved.

Referring to FIG. 2, the assembly 1 is configured to be delivered to the target location via a positioning and extension instrument 10. In the preferred embodiment, the instrument 10 comprises a blood flow catheter 11, a plurality of expansion means, such as balloons 12, 13, 14, and a sheath 9 for maintaining the portions 4 and the elements 5 of the valve prosthesis 1 in a contraction position. The catheter 11 comprises a distal opening 1 1a permitting blood flow past the assembly 1 during implantation thereof. The catheter 11 may further comprise a pump facilitating this blood flow.

Referring to FIG. 4, in the preferred embodiment, the distal balloon 12 is in a truncated cone shape and is dimensioned for bearing against the flared wall 104 of the ventricle when it is inflated. Once inflated to engage the native lumen 104, the distal balloon 12 sealingly bears against the wall 104 so as to channel the ongoing flow of blood inside the catheter 11. In the case of the delivery device, the term distal shall refer to the end of the catheter distal from the clinician. In the case of the prosthesis, the term distal shall refer to the end farthest from the ventricle in the direction of blood flow. When positioned properly, the medial balloon 13 is configured to inflate relative to the base ring of the valve 3, pushing the proximal tubular portion 4 and the prosthesis base ring against the native valve annulus. The proximal balloon 14 of catheter 11 is configured to inflate relative to the distal tubular portion 4 of the prosthesis assembly 1.

Still referring to FIG. 4, the sheath 9 is configured to slide on the catheter 11 and can be withdrawn to permit expansion of the assembly 1 to expand into place. As shown, the medial balloon 13 is preferably inflated while the proximal tubular portion 4 is still housed within sheath 9. The balloon 13 is inflated until the portion 4 presses against the ring 101 and then rests against the median prongs of the fasteners 6 in order to make the fasteners 6 slide through the holes of the pallets 5b, thus inserting the side prongs of these fasteners 6 in this ring 101.

Once the anchoring of the proximal tubular portion 4 has been achieved, the sheath 9 is moved back so that the distal tubular portion 4, which is extended and anchored by means of the proximal balloon 14, can be deployed in the same manner. The expansion of the tubular portions 4 ensures expansion of the elements 5 and the valve 3 accordingly. The pliable structure of the portions 4 allows the latter to be adapted to the specific anatomy of the implantation site, particularly when the natural valve is not excised and/or when this valve or ring 101 presents calcified areas. The elements 5 allow the sufficient extension of the leaflets to be ensured, whatever the configuration of the tubular portions 4, following implantation. The space between individual elements 5 permit significant blood flow to the coronary ostia 103. Fasteners 6 ensure immobilization of assembly 1 at the implantation site and preclude migration. The fully implanted assembly 1 is shown in FIG. 6.

Figure 7:
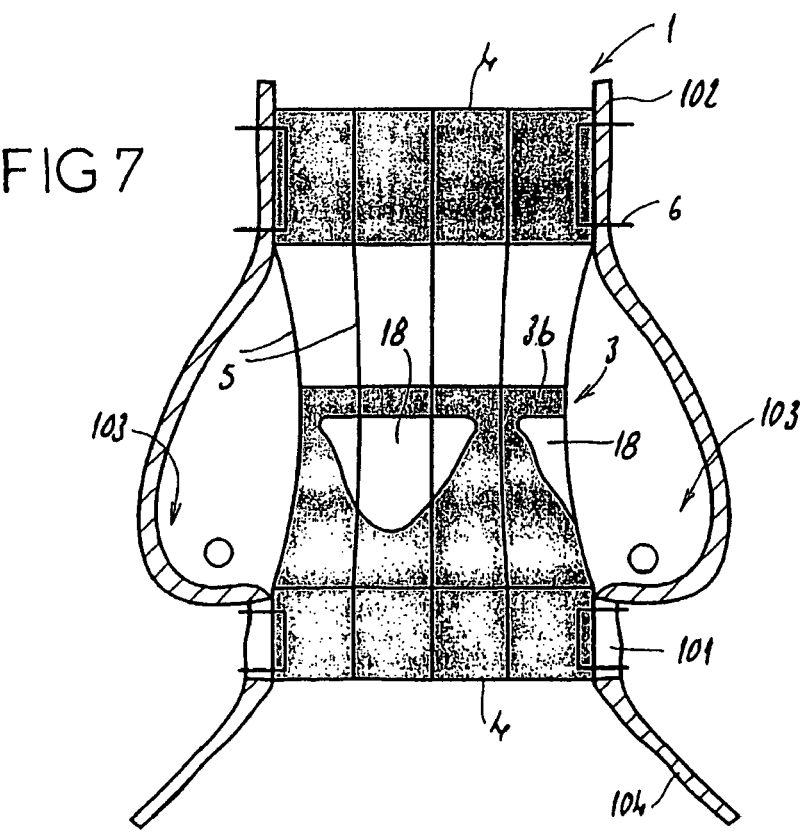
FIG. 7 is a schematic view of an alternative embodiment of the present valve assembly.

FIG. 7 shows an assembly 1 in which the valve 3 presents a peripheral wall 3b. This wall 3b is connected to the elements 5 and presents side openings 18, arranged between the leaflets, which allows the blood to flow to the coronary ostia 103. FIG. 8 shows an assembly 1 in which the proximal zone 4a of the proximal tubular portion 4 presents, or adopts by elastic deformation, a truncated cone shape suitable for bearing against the wall 104 of the ventricle. The balloon 12 causes the extension of this zone 4a.

It is contemplated that the pallets 5b and fasteners may comprise one of various configurations, as shown by example in FIGS. 9A to 17. FIGS. 9A to 13C specifically show the fasteners 6 implementing anchoring by plastic deformation. In one case, the holes of pallet 5b may be oriented obliquely, as for example in FIG. 9A, permitting an oblique extension of the anchoring prongs of the fastener 6, as shown for example, in FIG. 9B. Such oblique orientation may reinforce the resistance of the anchoring force. In other alternative arrangements, the median prong of the fasteners 6 may present a non-rectilinear form, either in a chevron configuration (see FIG. 10A) or wavy configuration (see FIG. 11A). When balloons 13, 14 are applied against such configuration, the anchoring prongs engage the native lumen in an oblique orientation, as shown in FIGS. 10B, 11B. Alternatively, the side prongs may be rectilinear (see FIGS. 9A to 10B) or curved (see FIGS. 11A, 11B). If desired, the fasteners 6 may be made of a shape-retaining material, particularly the nickel and titanium alloy known under the name "Nitinol." The anchoring prongs of these fasteners may then be rectilinear before anchoring (see FIG. 12A) and may take a curved form by shape retention (see FIG. 12B).

Referring to FIGS. 13 and 14, in other configurations, the fasteners 6 may be axially movable related to the pallet 5b by being guided with respect to the pallet to extend the anchoring prongs. This guiding may particularly be performed by engaging one or more fastener bases 6a comprising a "T-slot" arranged in the pallet 5b (see FIGS. 13A to 13C); these anchoring prongs may swivel and may be moved by bearing against the corresponding walls 15 of the pallet 5b (see FIGS. 13A, 13B), or may be bendable (see FIGS. 14A, 14B). Movement of these fasteners may be performed by expansion means, such as a balloon with a plurality of chambers inflated successively to axially push the fasteners 6 toward the extension position of their anchoring prongs.

Referring to FIGS. 15 and 16, the fasteners 6 may comprise a pad 16 and a plurality of perpendicular median prongs promoting a perpendicular compression in the wall. The pads 16 are configured so as to pushed against the native lumen by the expanding force of balloons 13, 14. Referring to FIG. 17, the fasteners 6 may be configured so as to be barbed.

Figure 18:
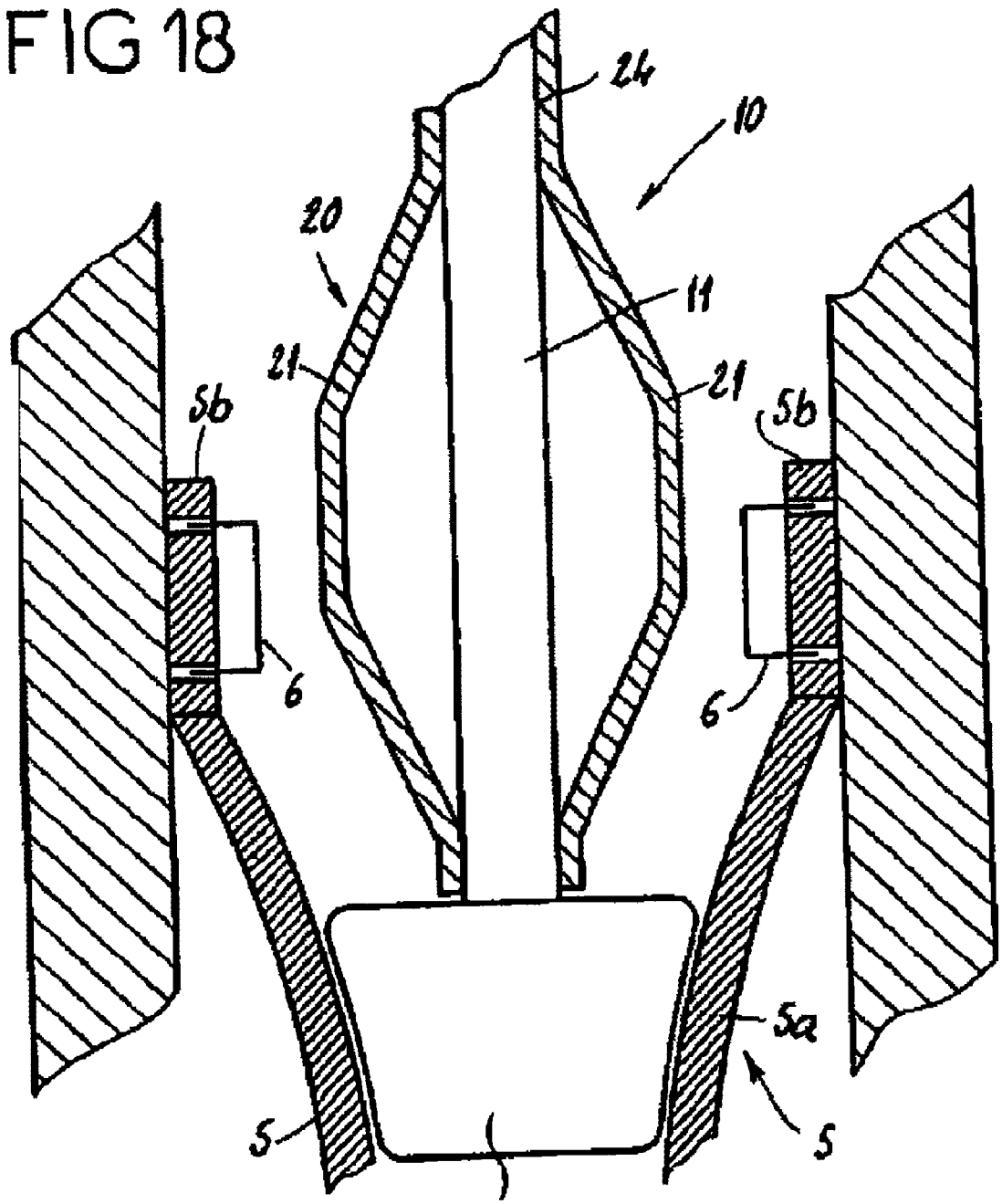
FIG. 18 is a schematic cross-sectional view of a portion of an alternative embodiment of the present inventive assembly showing extendable arms in the course of implanting the assembly.
Figure 19:
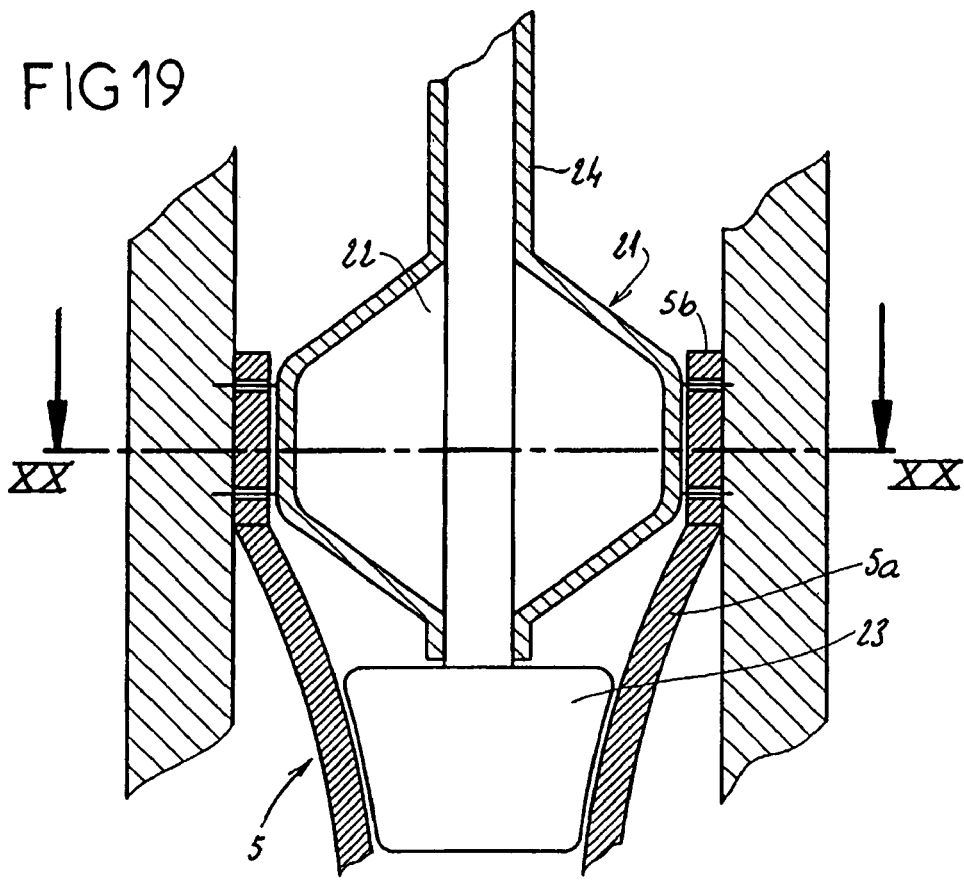
FIG. 19 is a schematic cross-sectional view of a portion of the embodiment of FIG. 18 showing the extendable arms fully extended.
Figure 20:
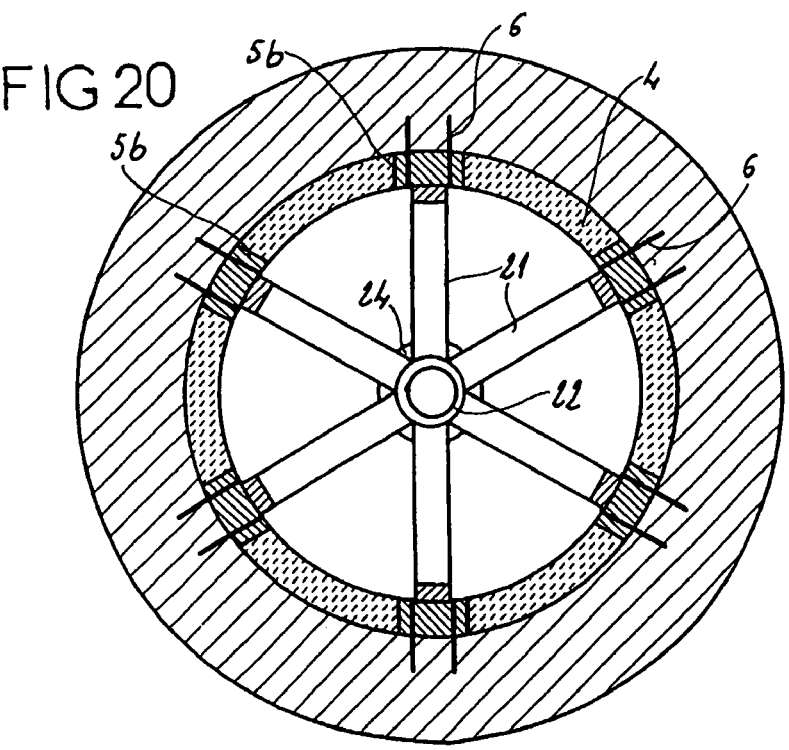
FIG. 20 is a cross sectional view of the assembly of FIG. 19 taken across line XX-XX.
Figure 21:
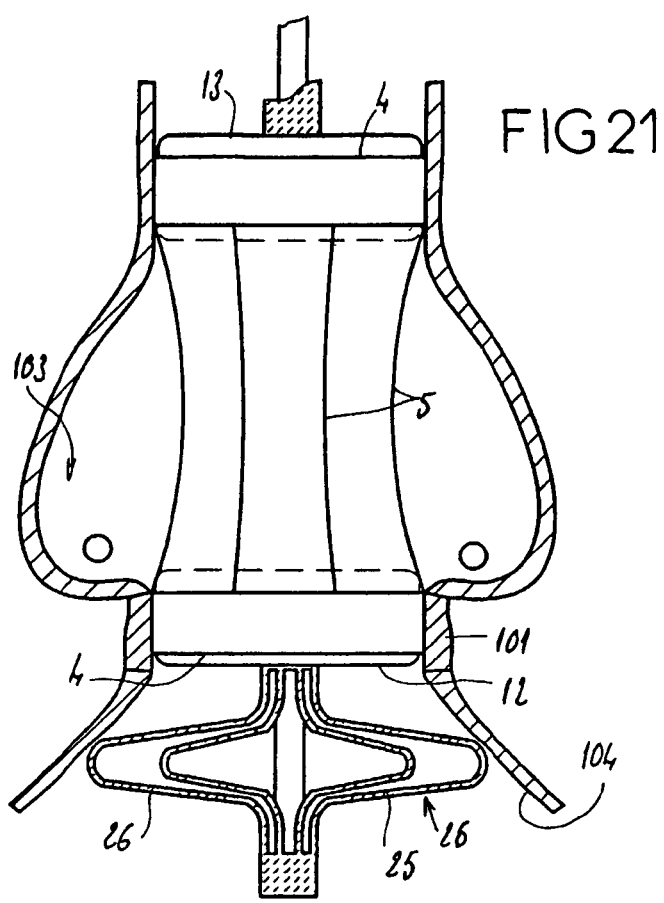
FIG. 21 is a schematic cross-sectional view of an alternative embodiment of the present invention.
Figure 22:
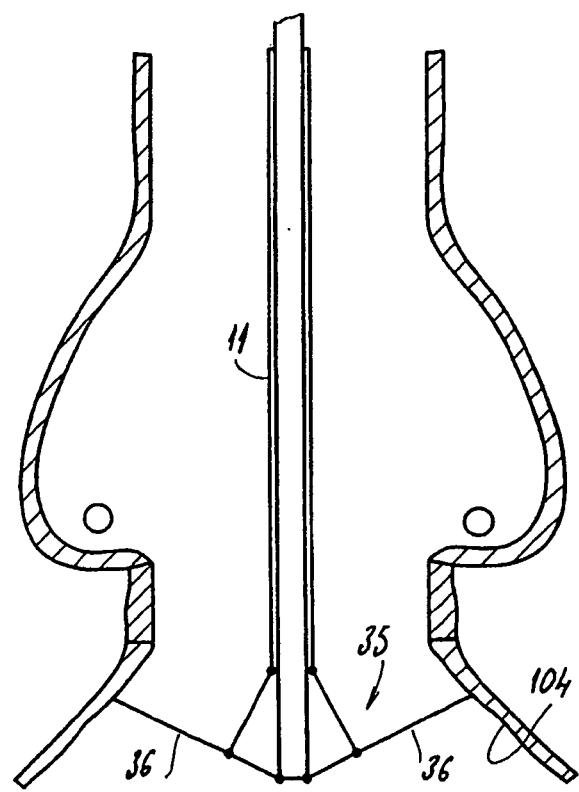
FIG. 22 is a schematic cross-sectional view of yet another alternative embodiment of the present invention.

Referring to FIGS. 18 to 20, the proximal balloon 14 may be replaced by radial extendable arms 21. In this alternative embodiment, the catheter 11 comprises a balloon 23 for extending the elements 5 and an inner sheath 24 linked on its proximal extremity to the catheter 11 but that may slide with respect to the latter outside of this extremity. This sheath 24 comprises longitudinal slots that space the arms 21 apart, and the sheath's sliding causes the radial extension of arms 21 by elastic deformation. Referring to FIG. 21, the distal balloon 12 may also be replaced by a similar structure 25 with radial extendable arms 26 similar to those described in reference to FIGS. 18 to 20. As shown in FIG. 22, the distal balloon 12 may also be replaced by a structure 35 that extends like an umbrella, the structure 35 comprising, for example, a series of ribs 36 for bearing against the wall 104.

Referring to FIG. 23, an assembly 1 comprises a support 2 that itself comprises a single tubular portion 4, from which the elongated reinforcing elements 5 protrude on an axial extremity of this tubular portion 4. The latter are rectilinear and of a limited length. In a manner similar to those described above, expansion of the valve 3 may be achieved.

The invention provides an assembly allowing the setting of a valve prosthesis in a corporeal duct, especially a cardiac valve and in particular an aortic valve, which presents determinant advantages compared to the homologous assemblies of the prior art. The invention is not limited to the form of embodiment described above by way of example but includes all the variations of embodiment within the scope of the claims below. Thus, for example, the elements 5 may comprise a rectilinear configuration naturally but be constrained during deployment by restraining means to create a medial inwardly curved profile, as shown above. The medial balloon 13 may also be replaced by radial extendable arms. Other proximal positioning means beyond those described herein, such as balloon 12, arms 25 or ribs 36, are contemplated. If so desired, the catheter 11 may also comprise a check valve.

What is claimed is:

1. A heart valve prosthesis assembly having a longitudinal axis and comprising an implantable valve and a valve support for supportably receiving the implantable valve, the implantable valve and the valve support being configured to contract for delivery and deployment and expand for implantation, the valve support comprising:
   a portion having an inner surface and an outer surface, said portion comprising a radially expandable pliable material, the radially expandable pliable material being slightly stretchable in the circumferential direction;
   a plurality of radially positioned anchoring prongs configured to anchor the heart valve prosthesis assembly to anatomy of the implantation site, the plurality of radially positioned anchoring prongs being configured to be inserted into the anatomy of the implantation site upon deployment of the heart valve prosthesis assembly; and
   a plurality of elongated reinforcing elements at least partially attached to the portion, the plurality of elongated reinforcing elements arranged on the outer surface of the portion, wherein each one of the plurality of elongated reinforcing elements are attached to the portion independently of one another.

2. The assembly of claim 1, wherein the plurality of radially positioned anchoring prongs are configured to not protrude outside of the outer radial surface of the portion before implantation of the heart valve prosthesis assembly.

3. The assembly of claim 1, wherein the plurality of radially positioned anchoring prongs are configured to be extendable for radial insertion into the anatomy of the implantation site.

4. The assembly of claim 1, wherein the plurality of radially positioned anchoring prongs are configured to be extendable for non-radial insertion into the anatomy of the implantation site.

5. The assembly of claim 4, wherein the plurality of radially positioned anchoring prongs are configured to be non-radially extendable for oblique orientation insertion into the anatomy of the implantation site.

6. The assembly of claim 1, wherein the plurality of radially positioned anchoring prongs penetrate the portion.

7. The assembly of claim 1, wherein the plurality of elongated reinforcing elements comprise at least two portions, wherein at least one of the portions defines a curved shape.

8. The assembly of claim 7, wherein at least one of the portions defines a convex shape with respect to the longitudinal axis of the heart valve prosthesis assembly.

9. The assembly of claim 7, wherein at least one of the remaining portions is substantially straight.

10. The assembly of claim 9, wherein at least one of the remaining portions is substantially straight with respect to the longitudinal axis of the heart valve prosthesis assembly.

11. The assembly of claim 9, wherein the plurality of elongated reinforcing elements are attached to the portion at the substantially straight portion of the plurality of elongated reinforcing elements.

12. The assembly of claim 9, wherein the plurality of radially positioned anchoring prongs penetrate the substantially straight portion of the plurality of elongated reinforcing elements.

13. The assembly of claim 1, wherein the plurality of elongated reinforcing elements are configured to expand to a predetermined diameter that substantially ensures sufficient expansion of the implantable valve.

14. The assembly of claim 1, wherein at least one of the plurality of radially positioned anchoring prongs is attached to at least one of the plurality of elongated reinforcing elements.

15. The assembly of claim 1, further comprising a second portion spaced from the portion by the plurality of elongated reinforcing elements.

16. The assembly of claim 15, wherein the valve support further comprises a median zone located between the portion and the second portion, the median zone having a smaller diameter than the diameters of the portion and the second portion.

17. The assembly of claim 15, wherein at least part of the implantable valve is located within the second portion, at least part of the second portion configured to be implanted in the proximal position with respect to the flow of blood through the assembly.

18. The assembly of claim 1, wherein the portion is substantially tubular.

19. The assembly of claim 1, wherein the heart valve prosthesis assembly is configured to permit lateral blood flow to the coronary ostia.

20. The assembly of claim 1, wherein the portion is configured to be expanded at a target location to provide a seal between the portion and the anatomy of the implantation site.

21. The assembly of claim 1, wherein the implantable valve is connected to the plurality of elongated reinforcing elements.

22. The assembly of claim 1, wherein the plurality of elongated reinforcing elements are plastically deformable.

23. The assembly of claim 1, wherein the plurality of radially positioned anchoring prongs comprise a shape-retaining material.

24. The assembly of claim 1, wherein the plurality of radially positioned anchoring prongs comprise a nickel and titanium alloy.

25. The assembly of claim 1, wherein the plurality of elongated reinforcing elements comprise a rectilinear form at rest and wherein the assembly further comprises restraining means to limit the radial expansion of at least a portion of the plurality of elongated reinforcing elements when expanded in place.

26. The assembly of claim 1, further comprising means for delivering and deploying said assembly.

27. The assembly of claim 26, wherein the delivering and deploying means comprises a catheter.

28. The assembly of claim 27, wherein the delivering and deploying means further comprises a sheath for maintaining the portion and the plurality of elongated reinforcing elements in a contracted configuration during delivery and at least one balloon for expanding the portion and the plurality of elongated reinforcing elements upon deployment.

29. The assembly of claim 27, wherein the delivering and deploying means further comprises a proximal positioning means, dimensioned for bearing against the anatomy of the implantation site.

30. The assembly of claim 27, wherein the catheter comprises a blood flow catheter, the blood flow catheter having a distal opening permitting blood flow past the assembly during implantation.

\* \* \* \* \*